US012116602B2

(12) United States Patent
Geng et al.

(10) Patent No.: US 12,116,602 B2
(45) Date of Patent: Oct. 15, 2024

(54) BUTYRYLCHOLINESTERASES HAVING AN ENHANCED ABILITY TO HYDROLYZE ACYL GHRELIN

(71) Applicant: Mayo Foundation for Medical Education and Research, Rochester, MN (US)

(72) Inventors: Liyi Geng, Rochester, MN (US); Ping Chen, Rochester, MN (US); William S. Brimijoin, Rochester, MN (US); Yang Gao, Rochester, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 91 days.

(21) Appl. No.: 17/930,943

(22) Filed: Sep. 9, 2022

(65) Prior Publication Data
US 2023/0193226 A1 Jun. 22, 2023

Related U.S. Application Data

(62) Division of application No. 16/373,444, filed on Apr. 2, 2019, now Pat. No. 11,473,069, which is a division of application No. 15/307,665, filed as application No. PCT/US2015/028141 on Apr. 29, 2015, now Pat. No. 10,301,609.

(60) Provisional application No. 61/985,883, filed on Apr. 29, 2014.

(51) Int. Cl.
| C12N 9/18 | (2006.01) |
| C07K 14/00 | (2006.01) |
| C07K 14/575 | (2006.01) |
| C12N 7/00 | (2006.01) |
| C12N 15/86 | (2006.01) |
| A61K 35/76 | (2015.01) |
| A61K 35/761 | (2015.01) |
| A61K 38/00 | (2006.01) |
| A61K 38/22 | (2006.01) |
| A61K 48/00 | (2006.01) |
| C07H 21/04 | (2006.01) |
| C12N 15/861 | (2006.01) |
| C12N 15/864 | (2006.01) |

(52) U.S. Cl.
CPC ............... *C12N 9/18* (2013.01); *C07K 14/00* (2013.01); *C07K 14/5759* (2013.01); *C12N 7/00* (2013.01); *C12N 15/86* (2013.01); *C12Y 301/01008* (2013.01); *A61K 35/76* (2013.01); *A61K 35/761* (2013.01); *A61K 38/00* (2013.01); *A61K 38/2264* (2013.01); *A61K 48/00* (2013.01); *C07H 21/04* (2013.01); *C12N 15/861* (2013.01); *C12N 15/8645* (2013.01); *C12N 2750/14141* (2013.01); *C12N 2750/14143* (2013.01)

(58) Field of Classification Search
CPC ........ C12Y 301/01008; C07K 14/5759; C12N 15/86; C12N 9/18
See application file for complete search history.

(56) References Cited

U.S. PATENT DOCUMENTS

| 5,580,859 | A | 12/1996 | Felgner et al. |
| 5,589,466 | A | 12/1996 | Felgner et al. |
| 6,001,625 | A | 12/1999 | Broomfield et al. |
| 6,884,870 | B2 | 4/2005 | Hav et al. |
| 7,919,082 | B1 | 4/2011 | Zhan et al. |
| 8,399,644 | B1 | 3/2013 | Zhan et al. |
| 10,301,609 | B2 | 5/2019 | Geng et al. |
| 11,473,069 | B2 | 10/2022 | Geng et al. |
| 2004/0086976 | A1 | 5/2004 | Fleer et al. |
| 2004/0121970 | A1 | 6/2004 | Watkins et al. |
| 2008/0213281 | A1 | 9/2008 | Watkins et al. |
| 2010/0254994 | A1* | 10/2010 | Raso ............... C07K 16/26 530/331 |
| 2011/0160121 | A1 | 6/2011 | Brizzi et al. |
| 2013/0071394 | A1* | 3/2013 | Troyer .............. A61K 39/395 424/134.1 |
| 2014/0294926 | A1 | 10/2014 | Chang et al. |
| 2014/0378380 | A1 | 12/2014 | Brizzi et al. |
| 2016/0032005 | A1 | 2/2016 | Borg et al. |

(Continued)

FOREIGN PATENT DOCUMENTS

WO  WO 2002/064796  8/2002

OTHER PUBLICATIONS

Battisti et al., "Cholinesterase activities and biochemical determinations in patients with prostate cancer: influence of Gleason score, treatment and bone metastasis," Biomed Pharmacother., 66(4):249-255, 2012.

(Continued)

*Primary Examiner* — Tekchand Saidha
(74) *Attorney, Agent, or Firm* — Fish & Richardson P.C.

(57) ABSTRACT

This document provides butyrylcholinesterases having an enhanced ability to hydrolyze acyl ghrelin as well as nucleic acids encoding such butyrylcholinesterases. This document also provides methods and materials for treating obesity and/or aggression. For example, methods for administering a nucleic acid encoding a wild-type or mutant butyrylcholinesterase having the ability to hydrolyze acyl ghrelin to a mammal under conditions wherein the level of acyl ghrelin within the mammal is reduced, under conditions wherein the rate of body weight gain of the mammal is reduced, under conditions wherein the mammal's level of aggression is reduced, and/or under conditions wherein the mammal's rate of developing stress-induced tissue damage are provided.

10 Claims, 14 Drawing Sheets
Specification includes a Sequence Listing.

(56) References Cited

U.S. PATENT DOCUMENTS

2017/0051261 A1    2/2017    Geng et al.
2019/0284540 A1    9/2019    Geng et al.

OTHER PUBLICATIONS

Biberoglu et al., "The Proline-rich tetramerization peptides in equine serum butyrylcholinesterase," FEBS Journal, 279(20):3844-3858, Oct. 2012.
Bloomfield et al., 1999, A Geneseq Accession No. AAY59235, computer printout, pp. 9-11.
Boberg et al., "Copy Number variation in ACHE/EPHB4 (7q22) and in BCHE/MME (3q26) genes in sporadic breast cancer," Chem Biol Interact., 203(1):344-347, 2013.
Boberg et al., "Molecular forms of butyrylcholinesterase and obesity," Genet Mol Biol., 33(3):452-454, 2010.
Bryan et al., 2013, http://www.elsevierblogs.conn/currentconnnnents/?p=962, Implications of protein fold switching, p. 1-4.
Carlson & Cummings., "Prospects for an anti-ghrelin vaccine to treat obesity," Mol Interv., 6: 249-252, 2006.
Cataliotti et al., "Oral brain natriuretic peptide: a novel strategy for chronic protein therapy for cardiovascular disease," Trends Cardiovasc Med., 17(1):10-14, 2007.
Chen et al. "Plasma Bufyrylcholinesterase Regulates Ghrelin to Control Aggression," Proceedings of the National Academy of Sciences., 112(12):2251-2256, Mar. 24, 2015.
Chen et al., "Butyrylcholinesterase gene transfer in obese mice prevents postdieting body weight rebound by suppressing ghrelin signaling," Proc. Natl. Acad. Sci. U. S. A., Oct. 2017, 114(41):10960-10965.
Chen et al., "Butyrylcholinesterase regulates central ghrelin signaling and has an impact on food intake and glucose homeostasis," Int. J. Obes. (Lond)., Sep. 2017, 41(9):1413-1419.
Dantas et al., "Obesity and variants of the GHRL (ghrelin) and BCHE (butyrylcholinesterase) genes," (Translated from eng) Genet Mol Biol., 34(2):205-207 (in eng), 2011.
De Vriese & Delporte., "Ghrelin: a new peptide regulating growth hormone release and food intake," International J Biochem Cell Biol., 40(8):1420-1424, 2008.
De Vriese et al., "Ghrelin degradation by serum and tissue homogenates: identification of the cleavage sites," Endocrinology., 145(11):4997-5005, 2004.
De Vriese et al., "Influence of ghrelin on food intake and energy homeostosis," Curr Opin Clin Nutr Metab Care., 10:615-619, 2007.
Delhanty et al., "Ghrelin: the differences between acyl- and des-acyl ghrelin," Eur J Endocrinol., 167: 601-608, 2012.
Delporte., "Structure and physiological actions of Ghrelin scientifica," Scienti Hindawi Publishing Corporation., 2013:1-25, 2013.
Duysen et al., "The butyrylcholinesterase knockout mouse a research tool in the study of drug sensitivity, bio-distribution, obesity and Alzheimer's disease," Expert Opin Drug Metab Toxicol., 5(5):523-528, 2009.
Extended European Search Report in International Application No. EP15785281.5, dated Sep. 28, 2017, 9 pages.
Extended European Search Report in International Application No. EP20170076.2, dated Sep. 7, 2020, 11 pages.
Garry, "Serum cholinesterase variants: examination of several differential inhibitors, salts and buffers used to measure enzyme activity," Clin Chem., 17(3):183-91, Mar. 1971.
Geneseq Accession No. AEM22918, "Human butyrylcholinesterase protein sequence," dated Jun. 15, 2007, 2 pages.

Geng et al., "Gene Transfer of Mutant Mouse Cholinesterase Provides High Lifetime Expression and Reduced Cocaine Responses with No Evident Toxicity," PLOS ONE., 8(6)e67446, 11 pages, 2013.
Guatelli et al., "Isothermal, in vitro amplification of nucleic acids by a multienzyme reaction modeled after retroviral replication," Proc Natl Acad Sci USA., 87(5):1874-1878, Mar. 1990.
International Preliminary Report on Patentability in International Application No. PCT/US2015/028141, Issued Nov. 1, 2016, 8 pages.
International Search Report and Written Opinion in International Application No. PCT/US2015/028141, Mailed Aug. 26, 2015, 11 pages.
International Search Report and Written Opinion in International Application No. PCT/US2017/51694, Mailed Nov. 28, 2017, 18 pages.
Kim et al., "Lifetime correction of genetic deficiency in mice with a single injection of helper-dependent adenoviral vector," Proc Natl Acad Sci USA., 98(23):13282-13287, Nov. 6, 2001.
Kobelt et al., "Anti-ghrelin Spiegelmer NOX-B11 inhibits neurostimulatory and orexigenic effects of peripheral ghrelin in rats," Gut, 55(6):788-792, Jun. 2006.
Kojima & Kangawa., "Ghrelin: Structure and Function," Physiol Rev., 85(2):495-522, 2005.
Kumar et al., "Serum butyrylcholineslerase and zinc in breast cancer," J Canc Res Ther., 13(2):367-370, 2017.
Laviano et al., "The Growth Hormone Secretagogue Receptor (Ghs-R)," Curr. Pharm. Design, 18(31):4749-4754, Sep. 2, 2012.
Li et al., The butyrylcholinesterase knockout mouse is obese on a high-fat diet. (Translated from eng) Chem Biol Interact., 175(1-3):88-91, 2008.
Maqbool et al., Biochem Soc Trans., 43(5):1011-1017, 2015.
Miller et al., "Amphiphilic conjugates of human brain natriuretic peptide designed for oral delivery: In vitro activity screening," Bioconjugate Chem., 17(2):267-274, Mar.-Apr. 2006.
Parks et al., "A helper-dependent adenovirus vector system: Removal of helper virus by Cre-mediated excision of the viral packaging signal," Proc Natl Acad Sci USA., 93:13565-13570, Nov. 1996.
Renee et al., "Tetramerization domain of human butyrylcholinesterase is at the C-terminus," Biochem J., 327(3): 747-757, Nov. 1, 1997.
Santarpia et al., "Butyrylcholineslerase as a prognostic marker: a review of the literature," J Cachexia Sarcopenia Muscle., 4(1):31-39, 2013.
Satou et al., 2010, Endocrinology, 151(10): 4765-4775.
Schwandt et al. "Differential Roles for Octanoylated and Decanoylated Ghrelins in Regulating Appetite and Metabolism," International J Peptides., 2010:1-7, 2010.
Tinoco et al. "Ghrelin Increases Food Intake, Swimming Activity and Growth in Juvenile Brown Trout (*Salmo trutta*)," Physiology & Behavior, 124:15-22, Oct. 30, 2013.
Tschop et al., "Ghrelin induces adiposity in rodents," Nature., 407(6806):908-913, Oct. 2000.
Veronese & Mero., "The impact of PEGylation on biological therapies," BioDrugs., 22(5):315-329, Sep. 2008.
Veronese & Pasut., "PEGylation, successful approach to drug delivery," Drug Discov Today., 10(21):1451-1458, Nov. 1, 2005.
Wang et al., "AlbuBNP, a recombinant B-type natriuretic peptide and human serum albumin fusion hormone, as a long-term therapy of congestive heart failure," Pharm Res., 21:2105-2111, 2004.
Watkins et al., 2004 (N_Geneseq Accession No. ADR01048, computer printout pp. 319-322).
Weiss., "Hot prospect for new gene amplifier," Science., 254(5036):1292, Nov. 29, 1991.
Xie et al., "An improved cocaine hydrolase: the A328Y mutant of human butyrylcholinesterase is 4-fold more efficient," Mol. Pharmacol., Jan. 1999, 55(1):83-91.

\* cited by examiner mouse BChE amino acid sequence (with 29aa signal peptide at N-terminus):

<u>METQHTKVTQTHFLLWILLLCMPFGKSHT</u>EEDFIITTKTGRVRGLSMPVLGGTVTAFLGIPYAQPPLGSLRFKKPQPLNK
WPDIHNATQYANSCYQNIDQAFPGFQGSEMWNPNTNLSEDCLYLNVWIPVPKPKNATVMVWIYGGGFQTGTSSLP
VYDGKFLARVERVIVVSMNYRVGALGFLAFPGNPDAPGNMGLFDQQLALQWVQRNIAAFGGNPKSITIFGESAGAAS
VSLHLLCPQSYPLFTRAILESGSSNAPWAVKHPEEARNRTLTLAKFTGCSKENEMEMIKCLRSKDPQEILRNERFVLPSDSI
LSINFGPTVDGDFLTDMPHTLLQLGKVKKAQILVGVNKDEGTAFLVYGAPGFSKDNDSLITRKEFQEGLNMYFPGVSRL
GKEAVLFYYVDWLGEQSPEVYRDALDDVIGDYNIICPALEFTKKFAELENNAFFYFFEHRSSKLPWPEWMGVMHGYEIE
FVFGLPLGRRVNYTRAEEIFSRSIMKTWANFAKYGHPNGTQGNSTMWPVFTSTEQKYLTLNTEKSKIYSKLRAPQCQF
WRLFFPKVLEMTGDIDETEQEWKAGFHRWSNYMMDWQNQFNDYTSKKESCTAL (SEQ ID NO:1)

mouse BChE coding sequence:

<u>ATG</u>GAGACTCAGCATACCAAGGTAACACAGACCCACTTCCTCCTATGGATTCTTCTGCTCTGCATGCCTTTTGGGAA
GTCACACACTGAAGAAGACTTCATAATTACAACCAAGACCGGAAGGGTCCGAGGGCTGAGCATGCCAGTTCTTGG
TGGCACGGTGACTGCCTTTCTCGGTATCCCCTATGCACAACCTCCTCTGGGTAGCCTAAGATTCAAAAAGCCGCAA
CCCTTAAACAAATGGCCTGACATCCATAATGCCACTCAATATGCAAATTCTTGTTATCAGAACATAGACCAAGCCTT
CCCAGGCTTCCAGGGGTCAGAAATGTGGAATCCAAACACAAACCTCAGTGAAGACTGCTTGTATCTGAATGTTTG
GATTCCAGTACCGAAGCCTAAAAATGCCACTGTCATGGTATGGATCTATGGTGGTGGCTTTCAAACTGGGACCTCT
TCTCTACCTGTTTACGATGGGAAGTTTCTAGCTCGTGTTGAAAGAGTTATTGTAGTTTCGATGAACTATAGGGTAG
GTGCTCTAGGATTCCTAGCTTTTCCCGGAAATCCCGATGCTCCAGGAAACATGGGTTTATTTGATCAACAGTTGGC
ACTTCAATGGGTCCAAAGAAATATAGCTGCTTTTGGAGGGAATCCTAAAAGTATAACGATTTTTGGAGAAAGTGCA
GGGGCAGCTTCAGTTAGCTTACATTTGCTCTGCCCCCAAAGTTATCCTTTGTTTACCAGAGCCATTCTTGAAAGTGG
CTCCTCTAATGCCCCCTGGGCAGTAAAGCATCCTGAGGAAGCCAGAAACAGAACCTTGACCTTAGCTAAATTTACT
GGTTGCTCAAAGGAAAATGAGATGGAGATGATTAAATGCCTTCGAAGTAAAGATCCTCAGGAAATTCTTCGCAAT
GAAAGGTTCGTTCTCCCCTCTGATTCCATCTTATCCATAAATTTTGGTCCAACAGTGGATGGCGATTTTCTCACCGAT
ATGCCCCACACACTACTCCAACTAGGAAAAGTGAAAAAAGCTCAGATCTTAGTGGGAGTTAACAAAGATGAAGGG
ACAGCTTTCCTAGTGTACGGTGCTCCGGGTTTCAGCAAAGACAATGATAGCCTTATCACAAGGAAGGAATTTCAAG
AAGGTTTAAATATGTATTTCCCTGGAGTGAGCAGATTGGGCAAGGAAGCAGTTCTTTTCTACTACGTGGACTGGTT
AGGTGAGCAGTCACCAGAAGTCTACCGTGACGCTTTGGATGATGTTATTGGAGATTACAACATCATCTGCCCTGCA
CTGGAGTTTACCAAGAAATTTGCAGAGCTTGAAAACAATGCTTTTTTCTACTTTTTCGAACATCGCTCTTCCAAACTA
CCTTGGCCGGAATGGATGGGAGTGATGCATGGCTATGAAATTGAATTTGTGTTTGGCTTACCTCTGGGAAGAAGA
GTTAATTATACGAGAGCTGAGGAAATCTTTAGTCGATCCATAATGAAAACTTGGGCAAATTTTGCAAAATATGGTC
ACCCCAATGGGACCCAGGGCAATAGCACAATGTGGCCTGTCTTCACAAGTACTGAACAAAAATACCTAACATTGAA
CACAGAGAAGTCAAAAATATACTCTAAACTTCGTGCTCCCCAATGTCAGTTCTGGAGACTATTTTTTCCAAAAGTCT
TGGAAATGACAGGAGATATTGATGAAACGGAGCAAGAGTGGAAGGCAGGATTTCATCGCTGGAGCAATTACATG
ATGGACTGGCAAAATCAATTTAACGATTACACTAGCAAGAAAGAGAGCTGTACAGCTCTC<u>TAA</u> (SEQ ID NO:2)

FIG. 1 human BChE amino acid sequence (with 28aa signal peptide at N-terminus):

<u>MHSKVTIICIRFLFWFLLLCMLIGKSHT</u>EDDIIIATKNGKVRGMNLTVFGGTVTAFLGIPYAQPPLGRLRFKKPQSLTKWS
DIWNATKYANSCCQNIDQSFPGFHGSEMWNPNTDLSEDCLYLNVWIPAPKPKNATVLIWIYGGGFQTGTSSLHVYDG
KFLARVERVIVVSMNYRVGALGFLALPGNPEAPGNMGLFDQQLALQWVQKNIAAFGGNPKSVTLFGESAGAASVSLH
LLSPGSHSLFTRAILQSGSFNAPWAVTSLYEARNRTLNLAKLTGCSRENETEIIKCLRNKDPQEILLNEAFVVPYGTPLSVN
FGPTVDGDFLTDMPDILLELGQFKKTQILVGVNKDEGTAFLVYGAPGFSKDNNSIITRKEFQEGLKIFFPGVSEFGKESILF
HYTDWVDDQRPENYREALGDVVGDYNFICPALEFTKKFSEWGNNAFFYYFEHRSSKLPWPEWMGVMHGYEIEFVFG
LPLERRDNYTKAEEILSRSIVKRWANFAKYGNPNETQNNSTSWPVFKSTEQKYLTLNTESTRIMTKLRAQQCRFWTSFFP
KVLEMTGNIDEAEWEWKAGFHRWNNYMMDWKNQFNDYTSKKESCVGL (SEQ ID NO:3)

human BChE coding sequence:

<u>ATG</u>CATAGCAAAGTCACAATCATATGCATCAGATTTCTCTTTTGGTTTCTTTTGCTCTGCATGCTTATTGGGAAGTCA
CATACTGAAGATGACATCATAATTGCAACAAAGAATGGAAAAGTCAGAGGGATGAACTTGACAGTTTTTGGTGGC
ACGGTAACAGCCTTTCTTGGAATTCCCTATGCACAGCCACCTCTTGGTAGACTTCGATTCAAAAAGCCACAGTCTCT
GACCAAGTGGTCTGATATTTGGAATGCCACAAAATATGCAAATTCTTGCTGTCAGAACATAGATCAAAGTTTTCCA
GGCTTCCATGGATCAGAGATGTGGAACCCAAACACTGACCTCAGTGAAGACTGTTTATATCTAAATGTATGGATTC
CAGCACCTAAACCAAAAAATGCCACTGTATTGATATGGATTTATGGTGGTGGTTTTCAAACTGGAACATCATCTTTA
CATGTTTATGATGGCAAGTTTCTGGCTCGGGTTGAAAGAGTTATTGTAGTGTCAATGAACTATAGGGTGGGTGCCC
TAGGATTCTTAGCTTTGCCAGGAAATCCTGAGGCTCCAGGGAACATGGGTTTATTTGATCAACAGTTGGCTCTTCA
GTGGGTTCAAAAAAATATAGCAGCCTTTGGTGGAAATCCTAAAAGTGTAACTCTCTTTGGAGAAAGTGCAGGAGC
AGCTTCAGTTAGCCTGCATTTGCTTTCTCCTGGAAGCCATTCATTGTTCACCAGAGCCATTCTGCAAAGTGGATCCT
TTAATGCTCCTTGGGCGGTAACATCTCTTTATGAAGCTAGGAACAGAACGTTGAACTTAGCTAAATTGACTGGTTG
CTCTAGAGAGAATGAGACTGAAATAATCAAGTGTCTTAGAAATAAAGATCCCCAAGAAATTCTTCTGAATGAAGCA
TTTGTTGTCCCCTATGGGACTCCTTTGTCAGTAAACTTTGGTCCGACCGTGGATGGTGATTTTCTCACTGACATGCC
AGACATATTACTTGAACTTGGACAATTTAAAAAAACCCAGATTTTGGTGGGTGTTAATAAAGATGAAGGGACAGCT
TTTTTAGTCTATGGTGCTCCTGGCTTCAGCAAAGATAACAATAGTATCATAACTAGAAAAGAATTTCAGGAAGGTT
TAAAAATATTTTTTCCAGGAGTGAGTGAGTTTGGAAAGGAATCCATCCTTTTTCATTACACAGACTGGGTAGATGA
TCAGAGACCTGAAAACTACCGTGAGGCCTTGGGTGATGTTGTTGGGGATTATAATTTCATATGCCCTGCCTTGGAG
TTCACCAAGAAGTTCTCAGAATGGGGAAATAATGCCTTTTTCTACTATTTTGAACACCGATCCTCCAAACTTCCGTG
GCCAGAATGGATGGGAGTGATGCATGGCTATGAAATTGAATTTGTCTTTGGTTTACCTCTGGAAAGAAGAGATAA
TTACACAAAAGCCGAGGAAATTTTGAGTAGATCCATAGTGAAACGGTGGGCAAATTTTGCAAAATATGGGAATCC
AAATGAGACTCAGAACAATAGCACAAGCTGGCCTGTCTTCAAAAGCACTGAACAAAAATATCTAACCTTGAATACA
GAGTCAACAAGAATAATGACGAAACTACGTGCTCAACAATGTCGATTCTGGACATCATTTTTTCCAAAAGTCTTGG
AAATGACAGGAAATATTGATGAAGCAGAATGGGAGTGGAAGCAGGATTCCATCGCTGGAACAATTACATGATG
GACTGGAAAAATCAATTTAACGATTACACTAGCAAGAAAGAAAGTTGTGTGGGTCTC<u>TAA</u> (SEQ ID NO:4)

FIG. 2

***(p<0.001 vs controls by 2-way ANOVA)

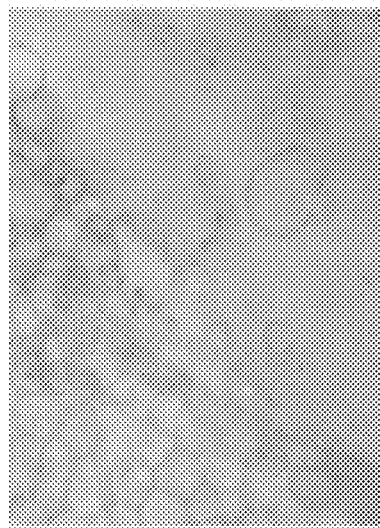
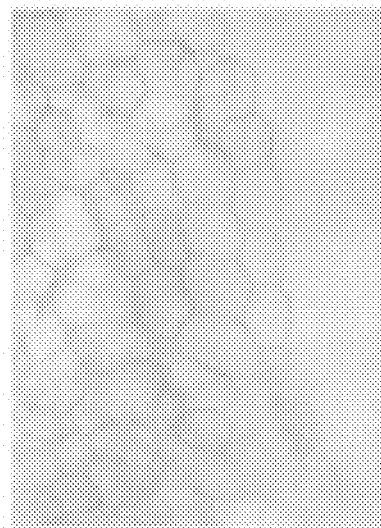
FIG. 13A  FIG. 13B
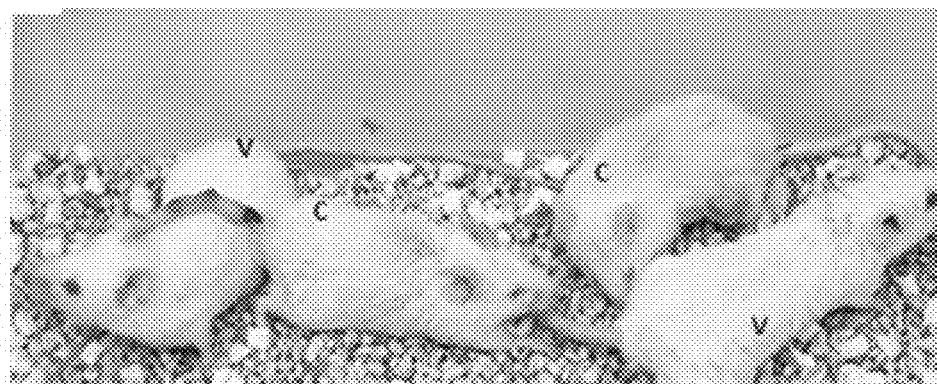
FIG. 13C

BUTYRYLCHOLINESTERASES HAVING AN ENHANCED ABILITY TO HYDROLYZE ACYL GHRELIN

CROSS REFERENCE TO RELATED APPLICATIONS

This application is a divisional application of U.S. Ser. No. 16/373,444, filed Apr. 2, 2019, which is a divisional application of U.S. Ser. No. 15/307,665, filed Oct. 28, 2016 (now U.S. Pat. No. 10,301,609), which is a National Stage application under 35 U.S.C. § 371 of International Application No. PCT/US2015/028141, having an International Filing Date of Apr. 29, 2015, which claims the benefit of U.S. Provisional Ser. No. 61/985,883 filed Apr. 29, 2014. This disclosures of the prior applications are considered part of (and are incorporated by reference in) the disclosure of this application.

SEQUENCE LISTING

This application contains a Sequence Listing that has been submitted electronically as an XML file named 07039-1327003_SL_ST26.xml. The XML file, created on Sep. 7, 2022, is 9325 bytes in size. The material in the XML file is hereby incorporated by reference in its entirety.

BACKGROUND

1. Technical Field

This document relates to butyrylcholinesterases (BChE) having an enhanced ability to hydrolyze acyl ghrelin as well as methods and materials for treating obesity and aggression. For example, this document provides nucleic acids encoding a butyrylcholinesterase having an enhanced ability to hydrolyze acyl ghrelin. In addition, this document provides methods and materials for using vectors (e.g., viral vectors) to express butyrylcholinesterases under conditions that reduce body weight within a mammal, reduce body weight gain in a mammal, reduce a mammal's level of aggression, reduce a mammal's response to cocaine, and/or reduce the severity of a stress-induced disability.

2. Background Information

Obesity is a medical condition where excess body fat accumulated to the extent that can cause a negative effect on health and/or lead to reduced life expectancy.

An aggressive behavior can be a behavior that is characterized by strong self-assertion with hostile or harmful tones. Aggressive behaviors can lead to various problems such as academic, employment, and relationship problems.

Stress-related disability is a growing problem in advanced countries with older populations.

SUMMARY

This document provides butyrylcholinesterases having an enhanced ability to hydrolyze acyl ghrelin. For example, this document provides nucleic acids that encode a butyrylcholinesterase polypeptide that (a) contains one or more amino acid mutations with respect to a wild-type butyrylcholinesterase polypeptide and (b) exhibits an elevated ability to hydrolyze acyl ghrelin with respect to the ability of that wild-type butyrylcholinesterase polypeptide. This document also provides methods and materials for treating obesity and/or aggression. For example, this document provides methods for administering a nucleic acid encoding a wild-type or mutant butyrylcholinesterase having the ability to hydrolyze acyl ghrelin to a mammal under conditions wherein the level of acyl ghrelin within the mammal is reduced, under conditions wherein the body weight of the mammal is reduced, under conditions wherein the body weight gain of the mammal is reduced, under conditions wherein the mammal's level of aggression is reduced, under conditions wherein the mammal's response to cocaine is reduced, and/or under conditions wherein the severity of a stress-induced disability is reduced. This document also provides methods for reducing stress-induced reactions by, for example, reducing the numbers of cells expressing "senescence-related markers" such as beta galactosidase.

As described herein, a nucleic acid can be designed to encode a polypeptide that includes the amino acid sequence set forth in FIG. 1 or the amino acid sequence set forth in FIG. 1 with one or more (e.g., two, three, four, five, or six) of the following amino acid substitutions: A199S, S227A, S287G, A328W, F329M, or Y332G (amino acid numbering starts after the signal sequence). In some cases, such a polypeptide can have an increased ability to hydrolyze acyl ghrelin as compared to a polypeptide having the amino acid sequence set forth in FIG. 1. In some cases, a nucleic acid can be designed to encode a polypeptide that includes the amino acid sequence set forth in FIG. 2 or the amino acid sequence set forth in FIG. 2 with one or more (e.g., two, three, four, five, or six) of the following amino acid substitutions: A199S, F227A, S287G, A328W, F329M, or Y332G (amino acid numbering starts after the signal sequence). In some cases, such a polypeptide can have an increased ability to hydrolyze acyl ghrelin as compared to a polypeptide having the amino acid sequence set forth in FIG. 2.

As also described herein, a wild-type or mutant butyrylcholinesterase or nucleic acid encoding a wild-type or mutant butyrylcholinesterase can be administered to a mammal (e.g., an obese human or an aggressive human) to reduce or control the body weight gain of that mammal, especially when, for example, that mammal has ready access to rich food (e.g., high calorie or high fat food), to reduce the aggressiveness of that mammal, and/or to reduce stress induced biochemical changes in body tissue. For example, a viral vector encoding a mutant butyrylcholinesterase having an enhanced ability to hydrolyze acyl ghrelin as compared to a wild-type human butyrylcholinesterase can be administered to a human to reduce the body weight of that human or to reduce the aggressiveness of that human or to protect that human from stress-related damage. In some cases, expression of a wild type or mutant BChE in vivo can reduce external and internal signs of aging and lower stress-induced tissue damage.

In general, one aspect of this document features a nucleic acid encoding a polypeptide having the amino acid sequence set forth in SEQ ID NO:3 with a F329M substitution (amino acid numbering starts after the signal sequence) or with a combination with one or more of the following amino acid substitutions: A199S, F227A, S287G, A328W, F329M, or Y332G (amino acid numbering starts after the signal sequence), wherein the polypeptide has an increased ability to hydrolyze acyl ghrelin as compared to a polypeptide having the amino acid sequence set forth in SEQ ID NO:3.

In another aspect, this document features a viral vector comprising a nucleic acid sequence that encodes a polypeptide having the amino acid sequence set forth in SEQ ID NO:3 with a F329M substitution (amino acid numbering starts after the signal sequence) or with a combination with one or more of the following amino acid substitutions: A199S, F227A, S287G, A328W, F329M, or Y332G (amino acid numbering starts after the signal sequence), wherein the polypeptide has an increased ability to hydrolyze acyl ghrelin as compared to a polypeptide having the amino acid sequence set forth in SEQ ID NO:3.

In another aspect, this document features a polypeptide having the amino acid sequence set forth in SEQ ID NO:3 with a F329M substitution (amino acid numbering starts after the signal sequence) or with a combination with one or more of the following amino acid substitutions: A199S, F227A, S287G, A328W, F329M, or Y332G (amino acid numbering starts after the signal sequence), wherein the polypeptide has an increased ability to hydrolyze acyl ghrelin as compared to a polypeptide having the amino acid sequence set forth in SEQ ID NO:3.

In another aspect, this document features a method for reducing the body weight of a mammal (e.g., a mammal having wild-type butyrylcholinesterase). The method comprises, or consists essentially of, administering a polypeptide or a nucleic acid encoding the polypeptide to the mammal, wherein the polypeptide comprises the ability to hydrolyze acyl ghrelin, and wherein the body weight of the mammal is reduced following the administration. The mammal can be a human. The method can comprise administering the polypeptide to the mammal. The method can comprise administering the nucleic acid to the mammal. The method can comprise administering a viral vector comprising the nucleic acid to the mammal. The viral vector can be an adeno-associated virus vector.

In another aspect, this document features a method for reducing the aggressiveness of a mammal (e.g., a mammal having wild-type butyrylcholinesterase). The method comprises, or consists essentially of, administering a polypeptide or a nucleic acid encoding the polypeptide to the mammal, wherein the polypeptide comprises the ability to hydrolyze acyl ghrelin, and wherein the aggressiveness of the mammal is reduced following the administration. The mammal can be a human. The method can comprise administering the polypeptide to the mammal. The method can comprise administering the nucleic acid to the mammal. The method can comprise administering a viral vector comprising the nucleic acid to the mammal. The viral vector can be an adeno-associated virus vector.

In another aspect, this document features a method for reducing the rate of aging in terms of external appearance and internal development of stress-induced tissue damage and biochemical and cellular changes characteristic of senescence in a mammal (e.g., a mammal having wild-type butyrylcholinesterase). The method comprises, or consists essentially of, administering a polypeptide or a nucleic acid encoding the polypeptide to the mammal, wherein the polypeptide comprises the ability to hydrolyze acyl ghrelin.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description below. Other features, objects, and advantages of the invention will be apparent from the description and drawings, and from the claims.

DESCRIPTION OF DRAWINGS

FIG. 1 is a sequence listing of a wild-type mouse butyrylcholinesterase (SEQ ID NO:1) along with a nucleic acid sequence (SEQ ID NO:2) that encodes this wild-type mouse butyrylcholinesterase.

FIG. 2 is a sequence listing of a wild-type human butyrylcholinesterase (SEQ ID NO:3) along with a nucleic acid sequence (SEQ ID NO:4) that encodes this wild-type human butyrylcholinesterase.

FIGS. 13A-13D. Photomicrographs of fat cells in 22-month-old mice. 13A) Fad pad sample from untreated control mouse. Blue stain=beta-galactosidase activity, classic sign of cellular aging and senescence. 13B) Sample from same-age mouse given adenoviral vector for mutant mouse butyrylcholinesterase at age 1 month. Absence of blue stain indicates healthy cells. 13C) photograph showing the external appearance of 16 month old mice from indicated groups (c=control, v=vector). 13D) Survival curve showing early death of controls housed for 5 months under conditions of moderate stress.

DETAILED DESCRIPTION

Figure 3A:
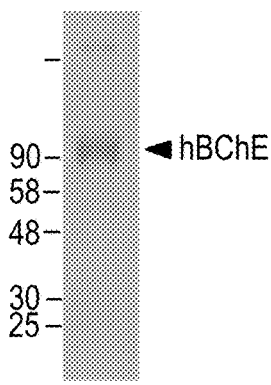
FIGS. 3A-3D. Deacylation of human ghrelin by human BChE. (3A) One µg of purified human BChE was analyzed by SDS-PAGE and stained with SYPRO-Ruby to confirm high purity (single major band). (3B) One ng of human acyl-ghrelin was treated with different amount of human BChE. After 20 hours of incubation, residual acyl ghrelin and desacyl ghrelin in each reaction were determined. (3C) One ng of human acyl ghrelin was treated with 10 µg of human BChE and % decrease in residual acyl ghrelin was measured as a function of time. (3D) Ten µg of human BChE was incubated for 10 minutes with 0, 10, or 100 µM of BChE inhibitor, iso-OMPA, or a proteinase inhibitor mixture containing 1 µM of aprotinin, 20 µM of leupeptin, and 15 mM of pepstatin A. Afterwards, 1 ng of human acyl ghrelin was added, and the reaction was incubated for 20 hours. The hydrolysis activities with butyrylthiocholine (BTCh) or acyl-ghrelin as substrates were determined by Ellman assay and acyl-ghrelin immunoassay, respectively. Data are normalized to the no inhibitor controls. All values are means±SD, each with duplicate samples (n=3).

This document provides butyrylcholinesterases having an enhanced ability to hydrolyze acyl ghrelin, nucleic acids encoding such butyrylcholinesterases, vectors (e.g., viral vectors) that contain nucleic acid encoding such butyrylcholinesterases, and methods and materials for treating obesity, aggression, or both. For example, this document provides nucleic acids encoding a butyrylcholinesterase having an enhanced ability to hydrolyze acyl ghrelin. In addition, this document provides methods and materials for using vectors (e.g., viral vectors) to express butyrylcholinesterases under conditions that reduce body weight gain within a mammal, that reduce a mammal's level of aggression, and/or that reduce stress that can lead to premature aging externally and internally, as well as increased risk of premature death. This document also provides methods and materials for using vectors to express wild type butyrylcholinesterases in greater than normal amounts under conditions that reduce body weight gain within a mammal, that reduce a mammal's level of aggression, and/or that reduce stress-induced tissue damage.

The polypeptides provided herein can be designed to include the amino acid sequence set forth in SEQ ID NO:1 or 3 or the amino acid sequence set forth in SEQ ID NO:1 or 3 with the exception that it contains one, two, three, four, five, or more amino acid additions, subtractions, or substitutions. For example, a polypeptide provided herein can have the amino acid sequence set forth in SEQ ID NO:3 with the following six changes: A199S, F227A, S287G, A328W, F329M, and Y332G. In some cases, a polypeptide provided herein can have the amino acid sequence set forth in SEQ ID NO:3 with a single F329M change. Other examples of polypeptides provided herein are set forth in Table 1. In some cases, a polypeptide provided herein can have an enhanced ability to hydrolyze acyl ghrelin as compared to a wild type human BChE having the amino acid sequence set forth in SEQ ID NO:3.

TABLE 1

Polypeptides based on human BChE.

| Mutations with respect to SEQ ID NO: 3 |
|---|
| A199S, F227A, S287G, and A328W |
| F329M |
| A199S, F227A, S287G, A328W, and F329M |

In some cases, a polypeptide provided herein can have an amino acid sequence with at least 85% (e.g., 85%, 86%, 87%, 88%, 89%, 90%, 91%, 92%, 93%, 94%, 95%, 96%, 97%, 98%, 99%, or 100%) sequence identity to a reference sequence (e.g., SEQ ID NO:1 or 3). In some cases, a polypeptide provided herein can have an amino acid sequence with at least 85% (e.g., 85%, 86%, 87%, 88%, 89%, 90%, 91%, 92%, 93%, 94%, 95%, 96%, 97%, 98%, 99%, or 100%) sequence identity to SEQ ID NO:1 or 3, provided that the amino acid sequence is not identical to the sequence set forth in SEQ ID NO:1 and 3. Percent sequence identity is calculated by determining the number of matched positions in aligned amino acid sequences (target amino acid sequence aligned to an identified amino acid sequence), dividing the number of matched positions by the number of amino acids of the identified amino acid sequence (e.g., SEQ ID NO:3), and multiplying by 100. A matched position refers to a position in which identical amino acids occur at the same position in aligned amino acid sequences. Percent sequence identity also can be determined for any nucleic acid sequence.

Percent sequence identity is determined by comparing a target amino acid sequence to the identified amino acid sequence (e.g., SEQ ID NO:3) using the BLAST 2 Sequences (B12seq) program from the stand-alone version of BLASTZ containing BLASTN version 2.0.14 and BLASTP version 2.0.14. This stand-alone version of BLASTZ can be obtained on the World Wide Web from Fish & Richardson's web site (fr.com/blast) or the U.S. government's National Center for Biotechnology Information web site (ncbi.nlm.nih.gov). Instructions explaining how to use the B12seq program can be found in the readme file accompanying BLASTZ.

B12seq performs a comparison between two sequences using either the BLASTN or BLASTP algorithm. BLASTN is used to compare nucleic acid sequences, while BLASTP is used to compare amino acid sequences. To compare two nucleic acid sequences, the options are set as follows: -i is set to a file containing the first nucleic acid sequence to be compared (e.g., C:\seq1.txt); -j is set to a file containing the second nucleic acid sequence to be compared (e.g., C:\seq2.txt); - p is set to blastn; - o is set to any desired file name (e.g., C:\output.txt); -q is set to -1; -r is set to 2; and all other options are left at their default setting. The following command will generate an output file containing a comparison between two sequences: C:\B12seq -i c:\seq1.txt -j c:\seq2.txt -p blastn -o c:\output.txt -q -1 -r 2. If the target sequence shares homology with any portion of the identified sequence, then the designated output file will present those regions of homology as aligned sequences. If the target sequence does not share homology with any portion of the identified sequence, then the designated output file will not present aligned sequences.

For example, if (1) a target sequence is compared to the sequence set forth in a reference sequence that has 100 amino acid residues and (2) the B12seq program presents the target sequence aligned with a region of that sequence with the number of matches being 86, then the amino acid target sequence has a percent identity to that reference sequence that is 86 (i.e., 86-100×100=86.0). It is noted that the percent identity value is rounded to the nearest tenth. For example, 78.11, 78.12, 78.13, and 78.14 are rounded down to 78.1, while 78.15, 78.16, 78.17, 78.18, and 78.19 are rounded up to 78.2. It also is noted that the length value will always be an integer.

A polypeptide provided herein can be produced using any suitable method, including recombinant technology. In some cases, a polypeptide provided herein can be a substantially pure polypeptide. As used herein, the term "substantially pure" with reference to a polypeptide means that the polypeptide is substantially free of other polypeptides, lipids, carbohydrates, and nucleic acid. In some cases, a substantially pure polypeptide can be a polypeptide that is at least 60 percent pure or is any chemically synthesized polypeptide. A substantially pure polypeptide can be at least about 60, 65, 70, 75, 80, 85, 90, 95, or 99 percent pure. Typically, a substantially pure polypeptide will yield a single major band on a non-reducing polyacrylamide gel.

In some cases, a polypeptide provided herein can be modified by linkage to a polymer such as polyethylene glycol (PEG), or by fusion to another polypeptide such as albumin, for example. For example, one or more PEG moieties can be conjugated to a polypeptide provided herein via lysine residues. Linkage to PEG or another suitable polymer, or fusion to albumin or another suitable polypeptide can result in a modified polypeptide having an increased half life as compared to an unmodified polypeptide. Without being bound by a particular mechanism, an increased serum half life can result from reduced proteolytic degradation, immune recognition, or cell scavanging of the modified polypeptide. Any appropriate method can be used to modify a polypeptide provided herein by linkage to PEG (also referred to as "PEGylation") or other polymers including, without limitation, those described elsewhere (U.S. Pat. No. 6,884,780; Cataliotti et al., *Trends Cardiovasc. Med.,* 17:10-14 (2007); Veronese and Mero, *BioDrugs,* 22:315-329 (2008); Miller et al., *Bioconjugate Chem.,* 17:267-274 (2006); and Veronese and Pasut, *Drug Discov. Today,* 10:1451-1458 (2005). Examples of methods for modifying a polypeptide provided herein by fusion to albumin include, without limitation, those described elsewhere (U.S. Patent Publication No. 20040086976, and Wang et al., *Pharm. Res.,* 21:2105-2111 (2004)).

Nucleic Acids, Vectors, and Host Cells

This document also provides nucleic acids encoding a polypeptide provided herein as well as expression vectors containing the nucleic acids, and host cells containing the nucleic acids and/or expression vectors. As used herein, the term "nucleic acid" refers to both RNA and DNA, including cDNA, genomic DNA, and synthetic (e.g., chemically synthesized) DNA. A nucleic acid molecule can be double-stranded or single-stranded (i.e., a sense or an antisense single strand). Nucleic acids include, for example, cDNAs encoding the chimeric polypeptides provided herein.

An "isolated nucleic acid" is a nucleic acid that is separated from other nucleic acid molecules that are present in a vertebrate genome, including nucleic acids that normally flank one or both sides of the nucleic acid in a vertebrate genome. The term "isolated" as used herein with respect to nucleic acids also includes any non-naturally-occurring nucleic acid sequence, since such non-naturally-occurring sequences are not found in nature and do not have immediately contiguous sequences in a naturally-occurring genome.

An isolated nucleic acid can be, for example, a DNA molecule, provided one of the nucleic acid sequences normally found immediately flanking that DNA molecule in a naturally-occurring genome is removed or absent. Thus, an isolated nucleic acid includes, without limitation, a DNA molecule that exists as a separate molecule (e.g., a chemically synthesized nucleic acid, or a cDNA or genomic DNA fragment produced by PCR or restriction endonuclease treatment) independent of other sequences as well as DNA that is incorporated into a vector, an autonomously replicating plasmid, a virus (e.g., a retrovirus, lentivirus, adenovirus, or herpes virus), or into the genomic DNA of a prokaryote or eukaryote. In addition, an isolated nucleic acid can include an engineered nucleic acid such as a DNA molecule that is part of a hybrid or fusion nucleic acid. A nucleic acid existing among hundreds to millions of other nucleic acids within, for example, cDNA libraries or genomic libraries, or gel slices containing a genomic DNA restriction digest, is not considered an isolated nucleic acid.

Isolated nucleic acid molecules can be produced using standard techniques, including, without limitation, common molecular cloning and chemical nucleic acid synthesis techniques. For example, polymerase chain reaction (PCR) techniques can be used to obtain an isolated nucleic acid containing a nucleotide sequence that encodes a BChE polypeptide. PCR refers to a procedure or technique in which target nucleic acids are enzymatically amplified. Sequence information from the ends of the region of interest or beyond typically is employed to design oligonucleotide primers that are identical in sequence to opposite strands of the template to be amplified. PCR can be used to amplify specific sequences from DNA as well as RNA, including sequences from total genomic DNA or total cellular RNA. Primers typically are 14 to 40 nucleotides in length, but can range from 10 nucleotides to hundreds of nucleotides in length. General PCR techniques are described, for example in PCR Primer: A Laboratory Manual, ed. by Dieffenbach and Dveksler, Cold Spring Harbor Laboratory Press, 1995. When using RNA as a source of template, reverse transcriptase can be used to synthesize complementary DNA (cDNA) strands. Ligase chain reaction, strand displacement amplification, self-sustained sequence replication, or nucleic acid sequence-based amplification also can be used to obtain isolated nucleic acids. See, for example, Lewis (1992) Genetic Engineering News 12:1; Guatelli et al. (1990) Proc. Natl. Acad. Sci. USA 87:1874-1878; and Weiss (1991) Science 254:1292.

Isolated nucleic acids also can be chemically synthesized, either as a single nucleic acid molecule (e.g., using automated DNA synthesis in the 3' to 5' direction using phosphoramidite technology) or as a series of oligonucleotides. For example, one or more pairs of long oligonucleotides (e.g., >100 nucleotides) can be synthesized that contain the desired sequence, with each pair containing a short segment of complementarity (e.g., about 15 nucleotides) such that a duplex is formed when the oligonucleotide pair is annealed. DNA polymerase is used to extend the oligonucleotides, resulting in a single, double-stranded nucleic acid molecule per oligonucleotide pair, which then can be ligated into a vector.

Isolated nucleic acids (e.g., nucleic acids encoding a polypeptide provided herein) also can be obtained by mutagenesis. For example, a reference sequence (e.g., SEQ ID NO:2 or 4) can be mutated using standard techniques including oligonucleotide-directed mutagenesis and site-directed mutagenesis through PCR. See, Short Protocols in Molecular Biology, Chapter 8, Green Publishing Associates and John Wiley & Sons, edited by Ausubel et al., 1992.

Vectors containing nucleic acids such as those described herein also are provided. A "vector" is a replicon, such as a plasmid, phage, or cosmid, into which another DNA segment may be inserted so as to bring about the replication of the inserted segment. An "expression vector" is a vector that includes one or more expression control sequences, and an "expression control sequence" is a DNA sequence that controls and regulates the transcription and/or translation of another DNA sequence.

In the expression vectors, a nucleic acid (e.g., a nucleic acid encoding a polypeptide provided herein) can be operably linked to one or more expression control sequences. As used herein, "operably linked" means incorporated into a genetic construct so that expression control sequences effectively control expression of a coding sequence of interest. Examples of expression control sequences include promoters, enhancers, and transcription terminating regions. A promoter is an expression control sequence composed of a region of a DNA molecule, typically within 100 to 500 nucleotides upstream of the point at which transcription starts (generally near the initiation site for RNA polymerase II). To bring a coding sequence under the control of a promoter, it is necessary to position the translation initiation site of the translational reading frame of the polypeptide between one and about fifty nucleotides downstream of the promoter. Enhancers provide expression specificity in terms of time, location, and level. Unlike promoters, enhancers can function when located at various distances from the transcription site. An enhancer also can be located downstream from the transcription initiation site. A coding sequence is "operably linked" and "under the control" of expression control sequences in a cell when RNA polymerase is able to transcribe the coding sequence into mRNA, which then can be translated into the protein encoded by the coding sequence.

Suitable expression vectors include, without limitation, plasmids and viral vectors derived from, for example, bacteriophage, baculoviruses, tobacco mosaic virus, herpes viruses, cytomegalovirus, retroviruses, vaccinia viruses, adenoviruses, and adeno-associated viruses. In some cases, a viral vector can be virus particles such as type five adenovirus, helper-dependent adenovirus, adeno associated virus, measles virus, or lentivirus virus particles that are designed to express a wild type BChE polypeptide or mutant BChE polypeptide provided herein. Numerous vectors and expression systems are commercially available from such corporations as Novagen (Madison, WI), Clontech (Palo Alto, CA), Stratagene (La Jolla, CA), and Invitrogen/Life Technologies (Carlsbad, CA).

An expression vector can include a tag sequence designed to facilitate subsequent manipulation of the expressed nucleic acid sequence (e.g., purification or localization). Tag sequences, such as green fluorescent protein (GFP), glutathione S-transferase (GST), polyhistidine, c-myc, hemagglutinin, or Flag™ tag (Kodak, New Haven, CT) sequences typically are expressed as a fusion with the encoded polypeptide. Such tags can be inserted anywhere within the polypeptide including at either the carboxyl or amino terminus.

This document also provides host cells containing a nucleic acid or vector provided herein. The term "host cell" is intended to include prokaryotic and eukaryotic cells into which a recombinant nucleic acid or vector (e.g., an expression vector) can be introduced. As used herein, "transformed" and "transfected" encompass the introduction of a nucleic acid molecule (e.g., a vector) into a cell by one of a number of techniques. Although not limited to a particular technique, a number of these techniques are well established within the art. Suitable methods for transforming and transfecting host cells can be found, for example, in Sambrook et al., Molecular Cloning: A Laboratory Manual ($2^{nd}$ edition), Cold Spring Harbor Laboratory, New York (1989). For example, calcium phosphate precipitation, electroporation, heat shock, lipofection, microinjection, and viral-mediated nucleic acid transfer can be used introduce nucleic acid into cells. In addition, naked DNA can be delivered directly to cells in vivo as described elsewhere (U.S. Pat. Nos. 5,580,859 and 5,589,466).

Compositions and Methods for Administration

A wild type BChE polypeptide or mutant BChE polypeptide provided herein, or a nucleic acid encoding a wild type BChE polypeptide or mutant BChE polypeptide provided herein, can be incorporated into a composition for administration to a mammal (e.g., an obese or aggressive human who is seeking treatment). For example, a viral vector designed to express a wild type BChE polypeptide or a mutant BChE polypeptide provided herein can be administered to a mammal (e.g., a human) under conditions wherein the body weight of the mammal, the rate of weight gain, and/or the level of aggressiveness of the mammal is reduced in a therapeutic manner. Compositions containing a wild type BChE polypeptide or mutant BChE polypeptide provided herein (or a nucleic acid encoding such a polypeptide) may be given once or more daily, weekly, monthly, or even less often, or can be administered continuously for a period of time (e.g., hours, days, or weeks). In some cases, preparations designed to stabilize such polypeptides may maintain effective activity in a mammal for several days. This document provides a viral vector or viral vectors designed to express a natural or mutant BChE polypeptide provided herein, which can be administered once to a mammal in a way that generates effective amounts of the polypeptide for months or years (e.g., two years or longer). In some cases, such treatment can be extended by later administration of an equivalent viral vector of altered serotype (e.g., type 8 adenoviral vector) to express the same polypeptide for extended treatments.

The polypeptide or nucleic acid to be administered to a mammal can be admixed, encapsulated, conjugated or otherwise associated with other molecules, molecular structures, or mixtures of compounds such as, for example, liposomes, receptor or cell targeted molecules, or oral, topical or other formulations for assisting in uptake, distribution and/or absorption. In some cases, a composition to be administered can contain a polypeptide or nucleic acid in combination with a pharmaceutically acceptable carrier. Pharmaceutically acceptable carriers include, for example, pharmaceutically acceptable solvents, suspending agents, or any other pharmacologically inert vehicles for delivering polypeptides, nucleic acids, or viral vectors (e.g., viral particles) to a subject. Pharmaceutically acceptable carriers can be liquid or solid, and can be selected with the planned manner of administration in mind so as to provide for the desired bulk, consistency, and other pertinent transport and chemical properties, when combined with one or more therapeutic compounds and any other components of a given pharmaceutical composition. Typical pharmaceutically acceptable carriers include, without limitation: water; saline solution; binding agents (e.g., polyvinylpyrrolidone or hydroxypropyl methylcellulose); fillers (e.g., lactose or dextrose and other sugars, gelatin, or calcium sulfate); lubricants (e.g., starch, polyethylene glycol, or sodium acetate);

disintegrates (e.g., starch or sodium starch glycolate); and wetting agents (e.g., sodium lauryl sulfate).

Acceptable solvents for delivery of viral vectors include, without limitation, common physiological salt solutions such as 0.9% sodium chloride, or isotonic aqueous solutions of sodium phosphate buffered to a pH of 7.4.

Pharmaceutical compositions containing a polypeptide, nucleic acid, or viral vector as described herein can be administered by a number of methods including by subcutaneous, intrathecal, intraventricular, intramuscular, intraperitoneal, or intravenous injection.

The invention will be further described in the following example, which does not limit the scope of the invention described in the claims.

EXAMPLES

Example 1—BChE Catalyzes Ghrelin Hydrolysis

Figure 3B:
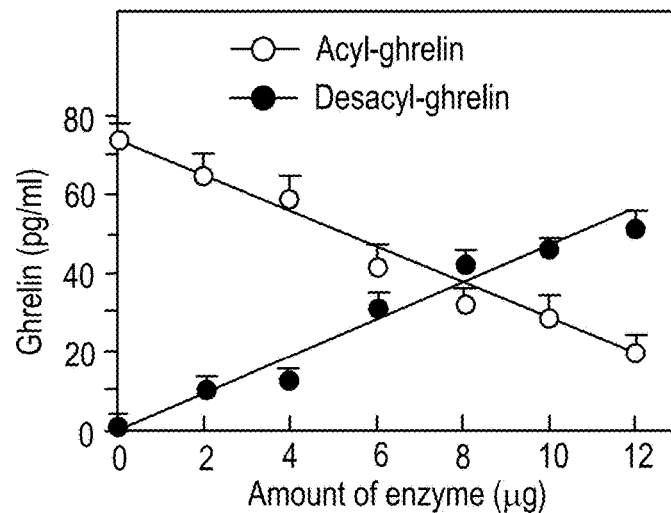
Figure 3C:
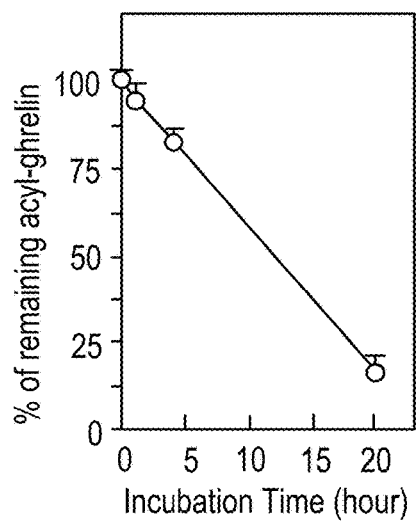
Figure 3D:
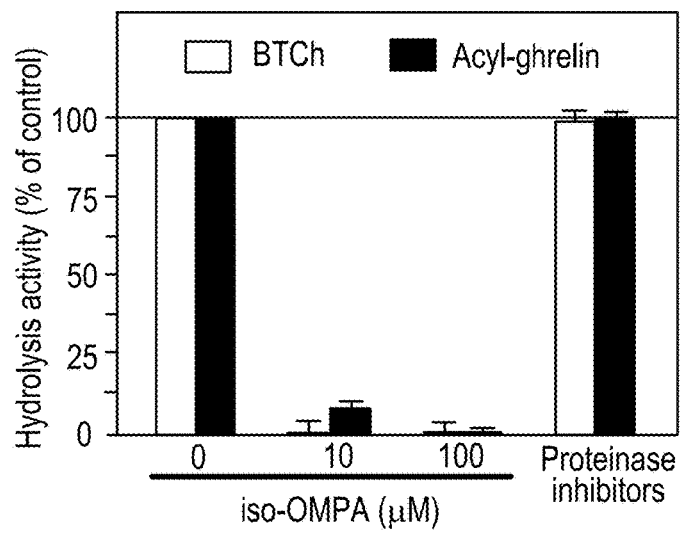

A sample of purified human BChE was obtained from Dr. O. Lockridge and assessed by gel electrophoresis (FIG. 3A). The enzyme preparation resulted in a primary band for monomeric BChE and a secondary band for dimeric BChE (FIG. 3A). No contaminants were detected. Incubation of a sample containing acyl ghrelin with increasing amounts of human BChE resulted in a decrease in the amount of acyl ghrelin and an increase in the amount of the breakdown product, desacyl ghrelin (FIG. 3B). A linear hydrolysis rate was observed (FIG. 3C). The hydrolysis of acyl ghrelin by human BChE was blocked by a BChE selective inhibitor (iso-OMPA) at the same concentration that blocks butyrylthiocholine (BTCh) hydrolysis (FIG. 3D). No inhibition of acyl ghrelin hydrolysis was observed using protease inhibitors (FIG. 3D). This is an example confirming that BChE has a well-developed capacity to metabolize ghrelin.

Example 2—In Vitro Screening Mutant Butyrylcholinesterases

Mutations of BChE

Human and mouse butyrylcholinesterase cDNAs were subjected to a series of amino acid substitutions in the region of the active site. Briefly, the steps were as follows. First, wild type mouse BChE cDNA or human BChE was cloned into a pAAV-CMV shuttle plasmid for a serotype 8 adenoassociated virus (AAV) gene transfer vector. A Kozak consensus sequence (GCCACC) was introduced before the translational start site. With this construct as template, site-directed mutagenesis using primers with specific base-pair alterations generated the desired sequences. The following mutants were made:

1. A328W (vs. human)
2. A328W/Y332A (vs. human)
3. F227A/S287G/A328W/Y332M (vs. human)
4. S227A/S287G/A328W/Y332M (vs. mouse)
5. A199S/A328W/Y332G (vs. human)
6. A199S/F227A/S287G/A328W/Y332G (vs. human BChE)
7. A199S/S227A/S287G/A328W/Y332G (vs. mouse BChE)
8. A199S/S287G/A328W/Y332A (vs. human)
9. F227A/S287G/A328W/Y332G (vs. human)
10. A199S/S287G/A328W/Y332A (vs. human)
11. F227A/S287G/A328W/Y332A (vs. human)
12. A199S/F227A/S287G/A328W/E441D (vs. human)
13. A199S/S227A/S287G/A328W/E441D (vs. mouse)
14. A199S/F227A/A328W/Y332G (vs. human)
15. A199S/F227A/S287G/A328W/Y332G/E441D (vs human)
16. A199S/S227A/S287G/A328W/Y332G/E441D (vs mouse)
17. F329M (vs. both)
18. A199S/F227A/S287G/A328W/F329M/Y332G (vs. human BChE)
19. A199S/S227A/S287G/A328W/F329M/Y332G (vs. mouse BChE)

Enzyme Screening Method

The A199S/F227A/S287G/A328W/Y332G (mutant human BChE) and the A199S/S227A/S287G/A328W/Y332G (mutant mouse BChE) enzymes were tested in vitro. For in vitro testing, HEK293 cells were transduced with AAV vector encoding the relevant enzyme cDNA, and enzyme was purified from culture supernatants by procainamide Sepharose column chromatography followed by ion-exchange chromatography. Purification led to a single major band on SDS polyacrylamide gel. Active sites were titrated with DFP to determine final molar enzyme concentration as described elsewhere (Geng et al., PloS-One, 8(6)e67446 (2013)). Samples were then tested with a commercial human ghrelin immunoassay kit to determine ghrelin hydrolyzing activity in vitro according to (a) a decrease in immunoreactive acyl ghrelin and (b) an increase in immunoreactive deacyl ghrelin.

The A199S/F227A/S287G/A328W/Y332G mutant human BChE exhibited modest activity, comparable to that of wild type human BChE, while the A199S/S227A/S287G/A328W/Y332G mutant mouse BChE exhibited enhanced activity (e.g., at least 20-fold more activity), comparable to that of wild type mouse BChE.

Example 3—Expression of a Mutant BChE In Vivo Reduces Acyl Ghrelin Levels and Increases Desacyl Ghrelin Levels Method for Viral Vector Delivery of Recombinant Butyrylcholinesterase to Mice Standard methods were used to introduce BChE cDNA into mice via hdAD and AAV viral gene transfer vectors. To produce and purify AAV8 viral particles, the plasmids pAAV-CMV-BChE (wt or mCocH) or pAAV-VIP-mCocH were co-transfected into HEK293T cells with helper vectors, pHelper and pAAV2/8, using FuGene HD Transfection Reagent (Roche). Three days later, AAV8 virus was purified from the cell lysates by ultracentrifugation against Optiprep Density Gradient Medium-Iodixanol (Sigma-Aldrich, St Louis MO). The concentration of viral particles was subsequently determined by real-time quantitative PCR (QPCR), which also was used to establish the tissue distribution of delivered vector.

Mutated BChE also was incorporated into a serotype-5 helper dependent adenoviral vector (hdAD) under regulation by a human ApoE hepatic control region (Kim et al., Proc. Natl. Acad. Sci. USA, 98:13282-13287 (2001)), with a bovine growth hormone polyadenylation sequence cloned into a derivative of the p281acZ hdAD-backbone plasmid. Vector was propagated using the AdNG163 helper virus as described elsewhere (Parks et al., Proc. Natl. Acad. Sci. USA, 93:13565-13570 (1996)). Particle titers were then determined by optical density at 260 nm. Helper virus contamination, determined by plaque assay on HEK-293 cells, was ~ 0.2% for both loaded and empty vectors.

Figure 4:
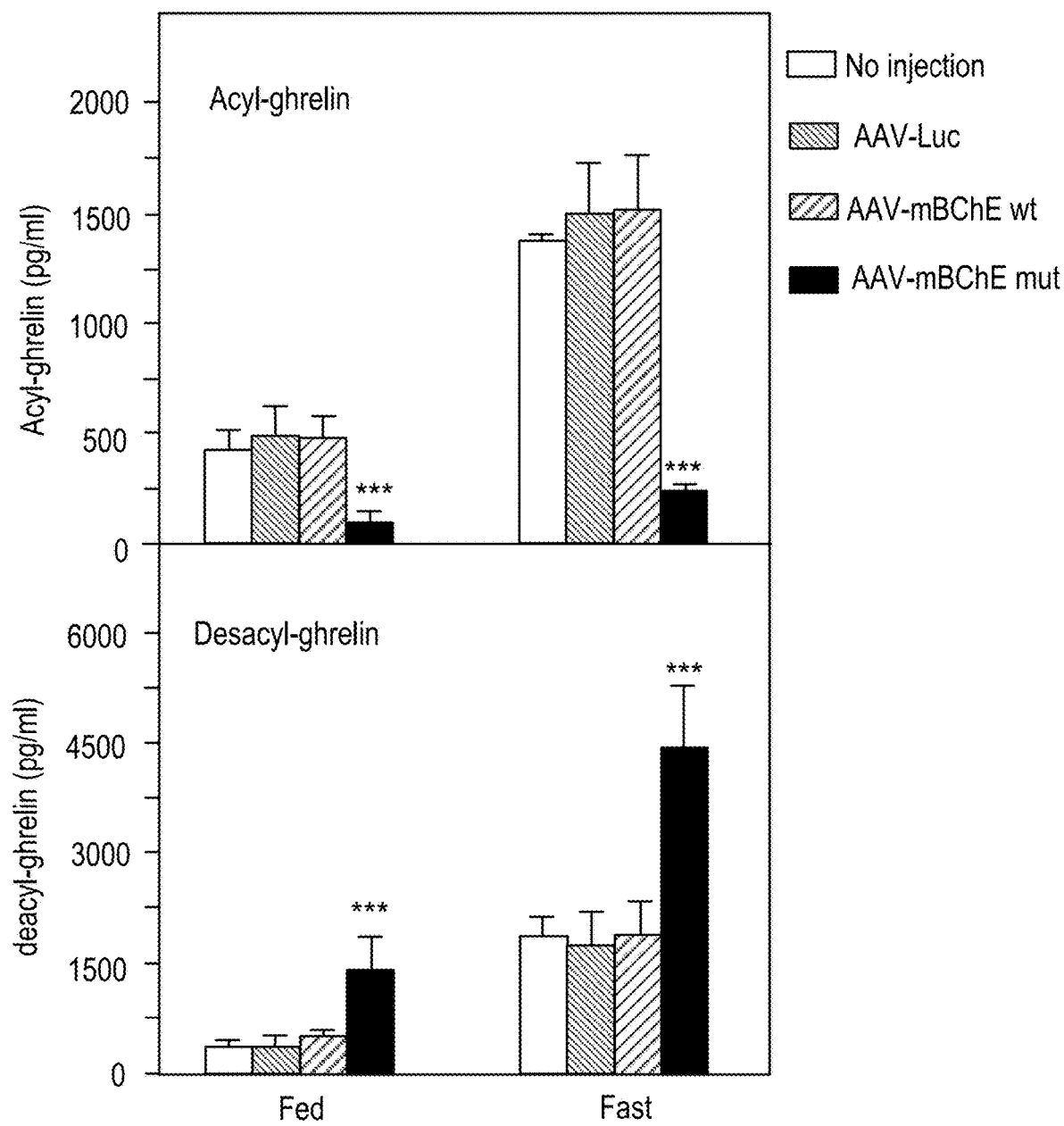
FIG. 4. Circulating levels of acyl-ghrelin and desacyl-ghrelin in mice with gene transfer of native mouse BChE (mBChE wt) or mutated enzyme (mBChE mut). C57bl/6 mice at 12-week age were fasted for 20 hours, and serum samples were collected to determine the levels of acyl ghrelin and desacyl ghrelin. Samples from ad libitum fed mice served as controls. All values are means+SD (n=5 per group), ***, p<0.001 compared with other groups.

Fed and fasting BALB/C mice (n=4) were injected with adeno-associated viral (AAV) vectors designed to express luciferase (control; AAV-Luc), wild-type mouse BChE (AAV-mBChE wt), or a mutant mouse BChE (AAV-mBChE mut). Uninjected mice (n=4) also were used as a control. The mutant mouse BChE had the sequence set forth in FIG. 1 with the following five amino acid substitutions: A199S/S227A/S287G/A328W/Y332G. Injection of AAV-mBChE mut resulted in a reduction in the plasma levels of acyl ghrelin and an increase in the plasma levels of desacyl ghrelin (FIG. 4). No significant effects were observed for the mice receiving AAV-Luc or AAV-mBChE wt (FIG. 4).

Figure 5:
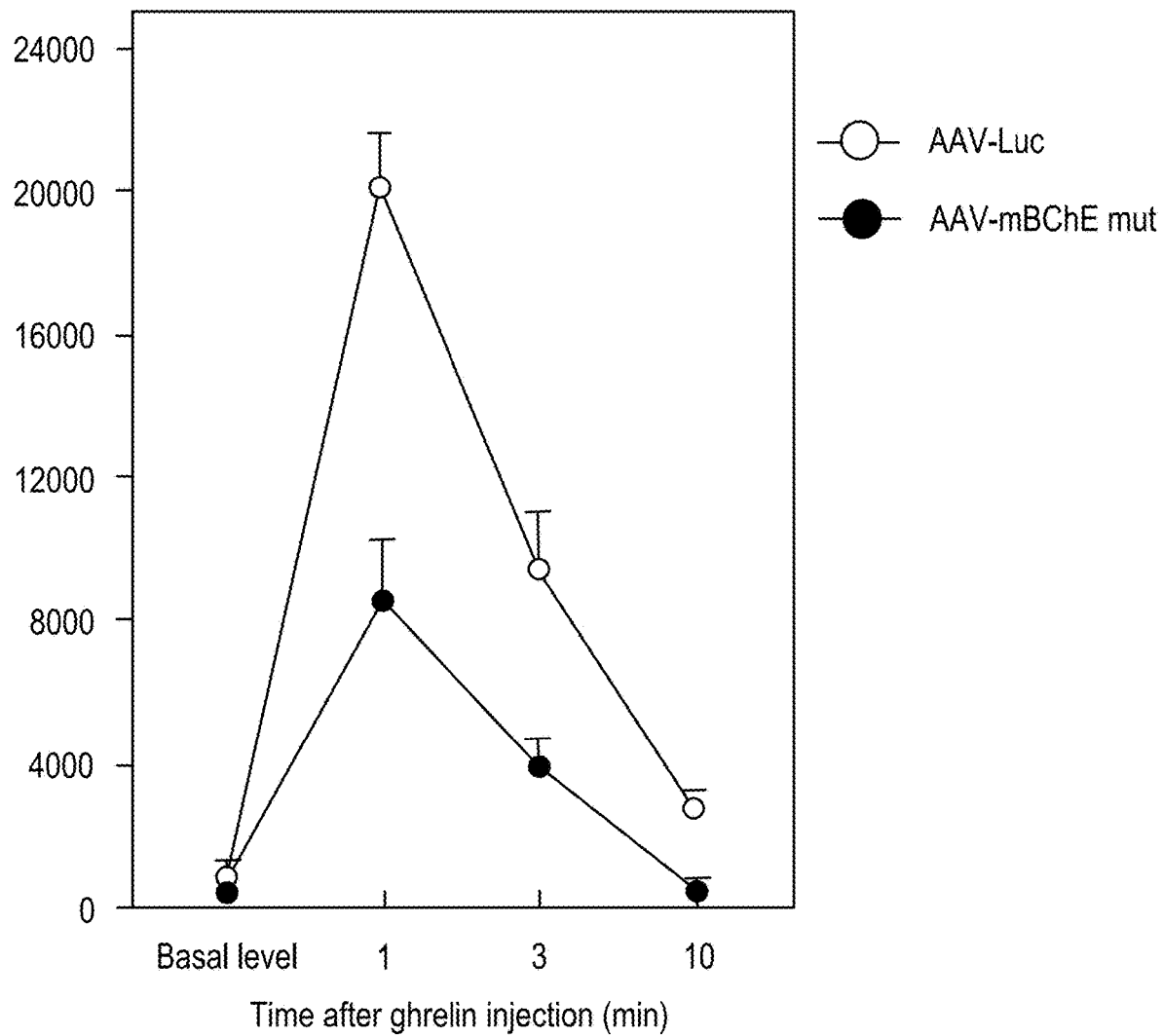
FIG. 5. Faster removal of ghrelin injected into mice with BChE gene transfer compared with a control gene transfer. Circulating acyl ghrelin levels after injection of 1 µg of recombinant human acyl ghrelin. Control 16-week old C57bl/6 mice and mice with gene transfer of AAV-Luc (control) or AAV-mBChE mut vector treatments were used. Acyl ghrelin levels in serum were determined 1, 3, and 10 minutes after injection. Serum samples from ad libitum fed mice served as basal levels. All values are means+SD (n=9).

In another experiment, mice injected with either AAV-Luc or AAV-mBChE mut were injected intravenously with exogenous acyl ghrelin peptide (1 mg/mouse), and the levels of acyl ghrelin in plasma were measured 1, 3, and 10 minutes later. Mice injected with AAV-mBChE mut exhibited an increased ability to eliminate acyl ghrelin from plasma (FIG. 5).

Figure 6A:
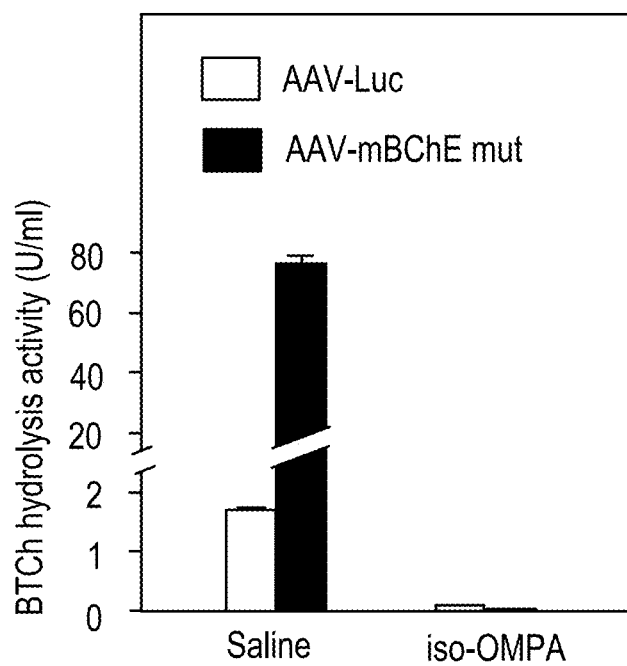
FIGS. 6A-6B. Selective inhibition of BChE increases acyl ghrelin levels in mice with AAV mBChE mut vector treatment. C57bl/6 mice with AAV-Luc or AAV-mBChE mut vector treatments (18-week old) received 40 mg kg-1 of selective BChE inhibitor (iso-OMPA) or saline. All mice were then fasted for 6 hours, and serum samples were collected to determine (6A) BChE activity versus the reference substrate (BTCh) and (6B) the levels of acyl ghrelin. All values are means+SD, each with duplicate samples (n=4), ***, p<0.001 compared with saline group.
Figure 6B:
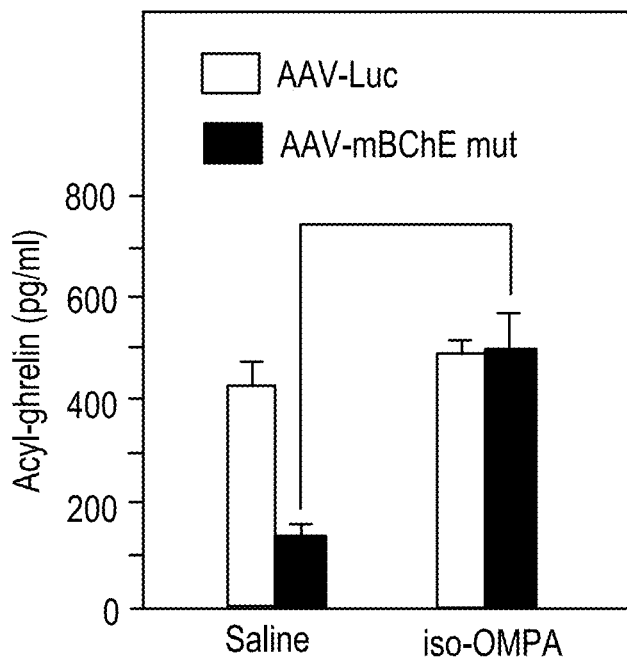

In another experiment, plasma obtained from mice injected with either AAV-Luc or AAV-mBChE mut followed by injection with either saline or iso-OMPA was assessed for the ability to hydrolyze BTCh in vitro. Treatment with iso-OMPA abolished the BTCh hydrolysis activity observed in samples from mice receiving AAV-mBChE mut in the absence of iso-OMPA (FIG. 6). In addition, the level of acyl ghrelin in plasma for AAV-mBChE mut-treated mice receiving iso-OMPA was equivalent to the level observed in AAV-Luc-treated control mice (FIG. 6). These results demonstrate that the reduced acyl ghrelin levels in mice receiving gene transfer of mutant BChE are specifically due to BChE-driven catalysis of the active peptide.

Figure 7:
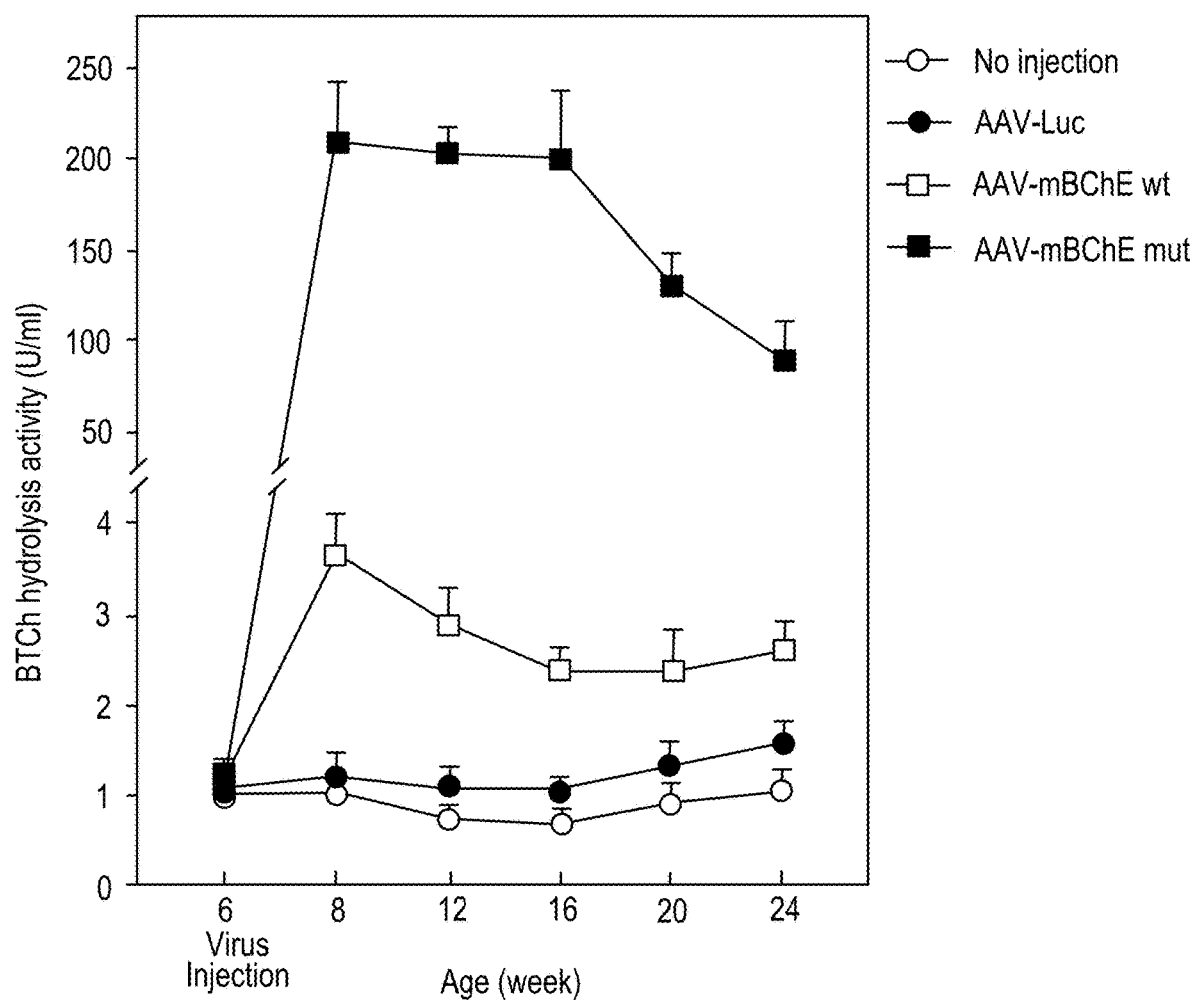
FIG. 7. Mouse models with high-expression levels of BChE by gene transfer. C57bl/6 mice were injected with AAV-Luc vector, AAV-mBChE wild type, or AAV-mBChE mutant vector at the dose of $1 \times 10^{13}$ viral particles per mouse at 6-week age. Plasma samples were collected at the indicated time points and assayed for BTCh hydrolysis activity. All values are means+SD, each with triplicate samples (n=5 per group).

In another experiment, C57bl/6 mice were injected with AAV-Luc vector, AAV-mBChE wild type, or AAV-mBChE mutant vector at the dose of $1 \times 10^{13}$ viral particles per mouse at 6-week age. Plasma samples were collected at the indicated time points and assayed for BTCh hydrolysis activity, which was much higher in the samples from mice given BChE vectors than in mice given the luciferase (control) vector (FIG. 7). All values are means+SD, each with triplicate samples (n=5 per group).

These results demonstrate that BChE is capable of inactivating ghrelin and that appropriate mutations in the BChE active site can cause large increases in peptide hydrolyzing activity. These results also demonstrate that a high activity mutant can be expressed indefinitely in mice after a single injection of viral vector (2 years or more) and that mice given such vector can have a 90% reduction in levels of active ghrelin in blood plasma with no detectable adverse effect. Further, injected exogenous ghrelin disappears much faster in vector-treated mice than in control mice, and selective inhibition of BChE can prevent accelerated ghrelin destruction and can raise ghrelin levels, but protease inhibitors have no such effect.

Figure 8A:
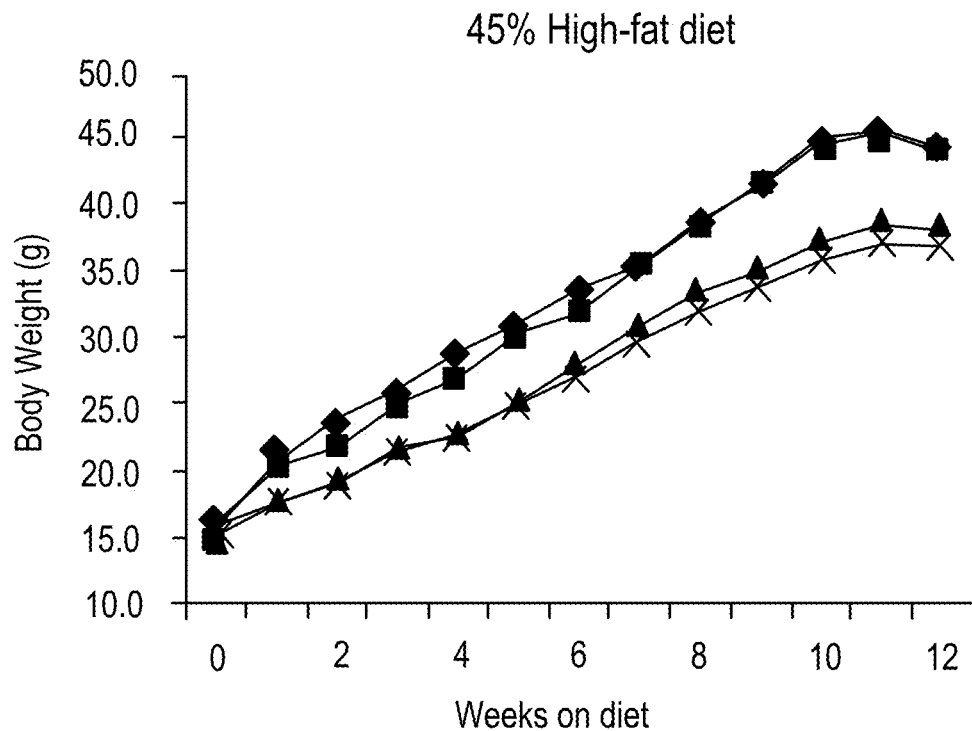
FIGS. 8A-8B are graphs plotting the weight gain of the indicated mice on normal diet (8B) and high fat (obesogenic) diet (8A).
Figure 8B:

Example 4—Expression of a Wild Type or Mutant BChE In Vivo Reduces Body Weight Gain Controls were C57BL6 mice treated with AAV luciferase vector or no injection. The experimental group received either AAV wild type mouse BChE vector or AAV mutant mouse BChE vector as indicated in Example 3. Two sets of experimental and control mice were tested for weight gain (n=5 to 8). One set received normal laboratory mouse diet. The other set received a high fat diet with 45% of calories from fat over the observation periods of 12 to 16 weeks. Results are provided in FIGS. 8A and 8B.

Example 5—Expression of Wild Type or Mutant BChE In Vivo Reduces Aggressive Behavior Controls were untreated or saline-treated mice (male Balb/C mice). The experimental group received the A199S/S227A/S287G/A328W/Y332G mutant mouse BChE by hdAD viral gene transfer (dose=$1.7 \times 10^{12}$ viral particles i.v.), delivered at about 6 weeks of age. The numbers of fights per session on successive trials in the standard "resident-intruder" model were scored by treatment-blind observer. Plasma BChE activity and ghrelin levels (pre-fight) also were recorded.

Figure 9:
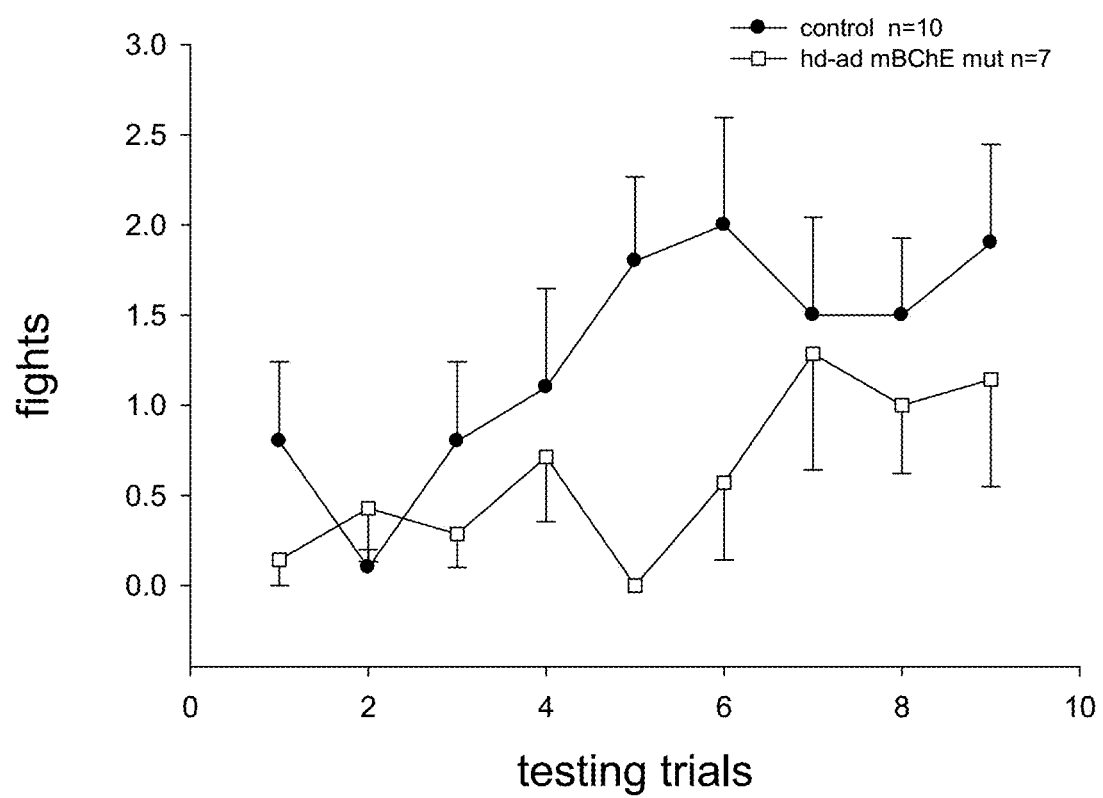
FIG. 9 is a graph plotting the number of fights per testing trial for the indicated mice.
Figure 10:
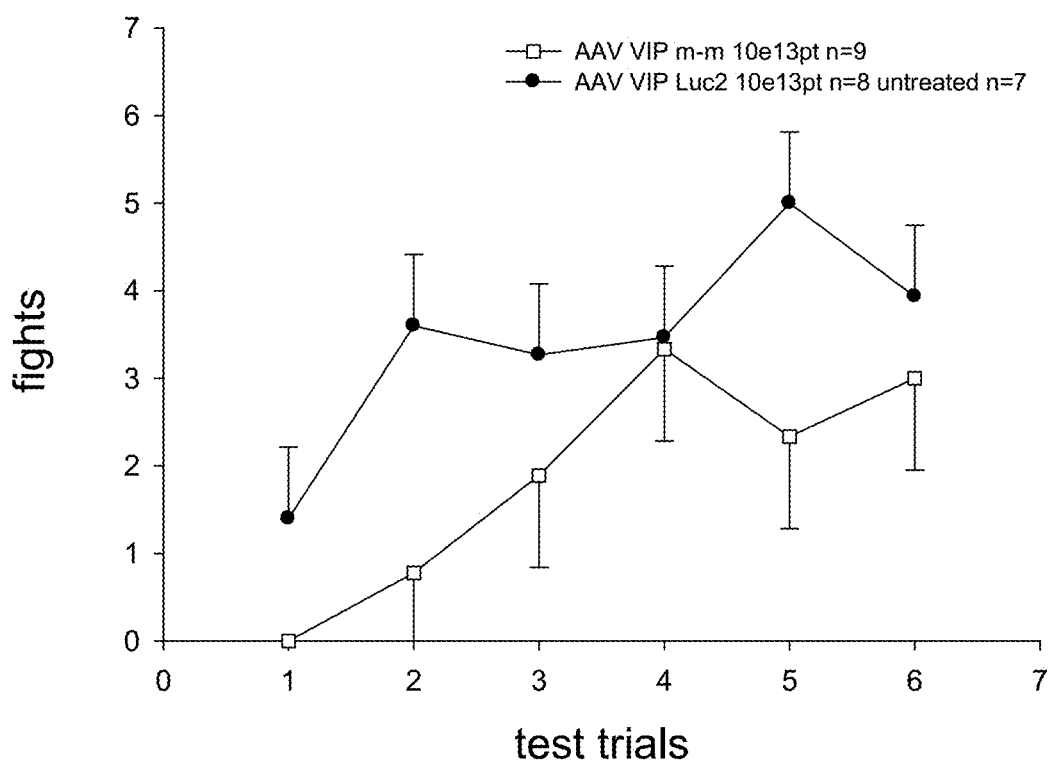
FIG. 10 is a graph plotting the number of fights per testing trial for the indicated mice.

Mice treated with the hdAD vector expressing mutant mouse BChE exhibited significantly reduced fighting compared with saline treated controls tested at 14-16 months of age (FIG. 9; p=0.003 by 2-way ANOVA). Mice treated with AAV vector encoding the same mutant mouse enzyme tested at 8 months of age also exhibited reduced fighting (FIG. 10; p=0.005). Plasma from these animals again revealed an about 100× increase in BChE levels and a substantial (50%) reduction in active ghrelin vs. saline controls and luciferase vector controls.

Figure 11:
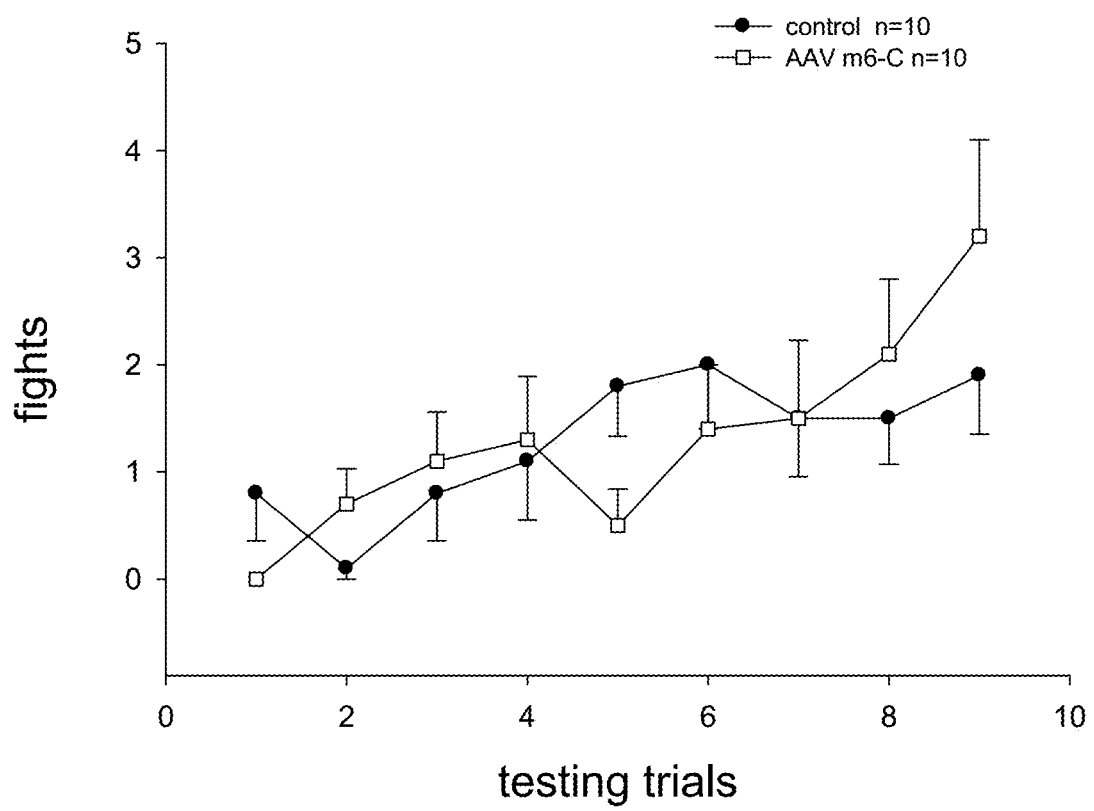
FIG. 11 is a graph plotting the number of fights per testing trial for the indicated mice.

To prove that reduced ghrelin caused the reduce aggression, mice were treated with a mutant human BChE ("Mut 6 with C terminal truncation) AAV VIP mut6-C (10e13pt/mouse, n=10) that was poor at inactivating ghrelin. These mice were assessed using the aggression test at 15 to 16 month and exhibited no group difference with control (FIG. 11). Plasma from these animals exhibited a large increase in BChE activity vs. butyrylthiocholine (94-fold above control) and cocaine (still larger increase), but no reduction of acyl ghrelin (only a non-significant 15% decrease). The enzyme assays revealed a nearly 100-fold increase in BChE and a 92% drop in active ghrelin 5 (Table 2). These results demonstrate that BChE-catalyzed loss of active ghrelin is involved in the anti-aggression effect of BChE gene transfer.

TABLE 2

Levels of active ghrelin (acyl ghrelin) and BChE activity in plasma samples collected at indicated ages from mice treated at about 6 weeks of age with the indicated viral gene-transfer expression vectors encoding the indicated enzymes. Controls received saline injections or vector encoding irrelevant protein (luciferase).

| Age | Vector treatment | n | Fasting acyl-ghrelin Mean (pg/ml) | % control | BChE level (U/mL) Mean (U/ml) | x-fold vs control |
|---|---|---|---|---|---|---|
| ~15 month | hd-AD Mut 1 m-BChE | 7 | 62 ± 8.9 | 7.7% | 60 ± 6.7 | 82 |
| ~15 month | Saline | 10 | 801 ± 310 | — | 0.7 ± 0.03 | |
| 10 month | AAV-8 Mut6- h-BChE | 10 | 177 ± 8.0 | 85% | 18 ± 3.5 | 94 |

TABLE 2-continued

Levels of active ghrelin (acyl ghrelin) and BChE activity in plasma samples collected at indicated ages from mice treated at about 6 weeks of age with the indicated viral gene-transfer expression vectors encoding the indicated enzymes. Controls received saline injections or vector encoding irrelevant protein (luciferase).

| Age | Vector treatment | n | Fasting acyl-ghrelin Mean (pg/ml) | % control | BChE level (U/mL) Mean (U/ml) | x-fold vs control |
|---|---|---|---|---|---|---|
| 10 month | saline | 13 | 210 ± 18 | — | 0.2 ± 0.06 | |
| 8 month | AAV-8 m-BChE | 5 | 78 ± 10 | 52% | 197 ± 23 | 123 |
| 8 month | Saline | 7 | 339 ± 59 | — | 1.6 ± 0.04 | |
| 3 month | None (BChE knockout) | | 910 ± 65 | 154% | 0.01 | 0% |
| 1 month | AAV-WT hBChE 3 × 10^12 | 5 | 308 ± 62 | 53% | 558 ± 183 | 299 |
| 1 month | AAV-F329M mut hBChE 3 × 10^12 | 2 | 109 ± 17* | 19% | 480 ± 77 | 257 |
| 1 month | AAV-F329M Mut mBChE 10^13 | 8 | 14 ± 8.5 | 8% | 592 ± 80 | 540 |
| 1 month | saline | 5 | 581 ± 120 | | 1.9 ± 0.27 | 1.9 |

Figure 12:
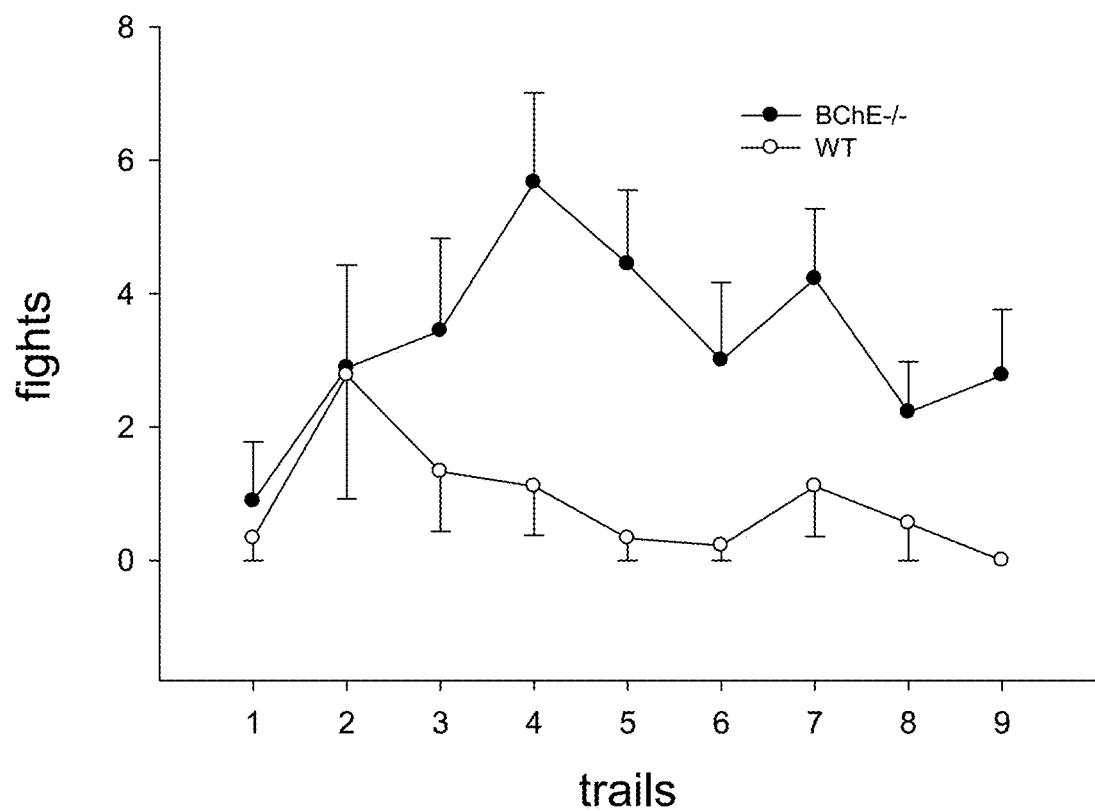
FIG. 12 is a graph plotting the number of fights per testing trial for the indicated mice.
Figure 13D:
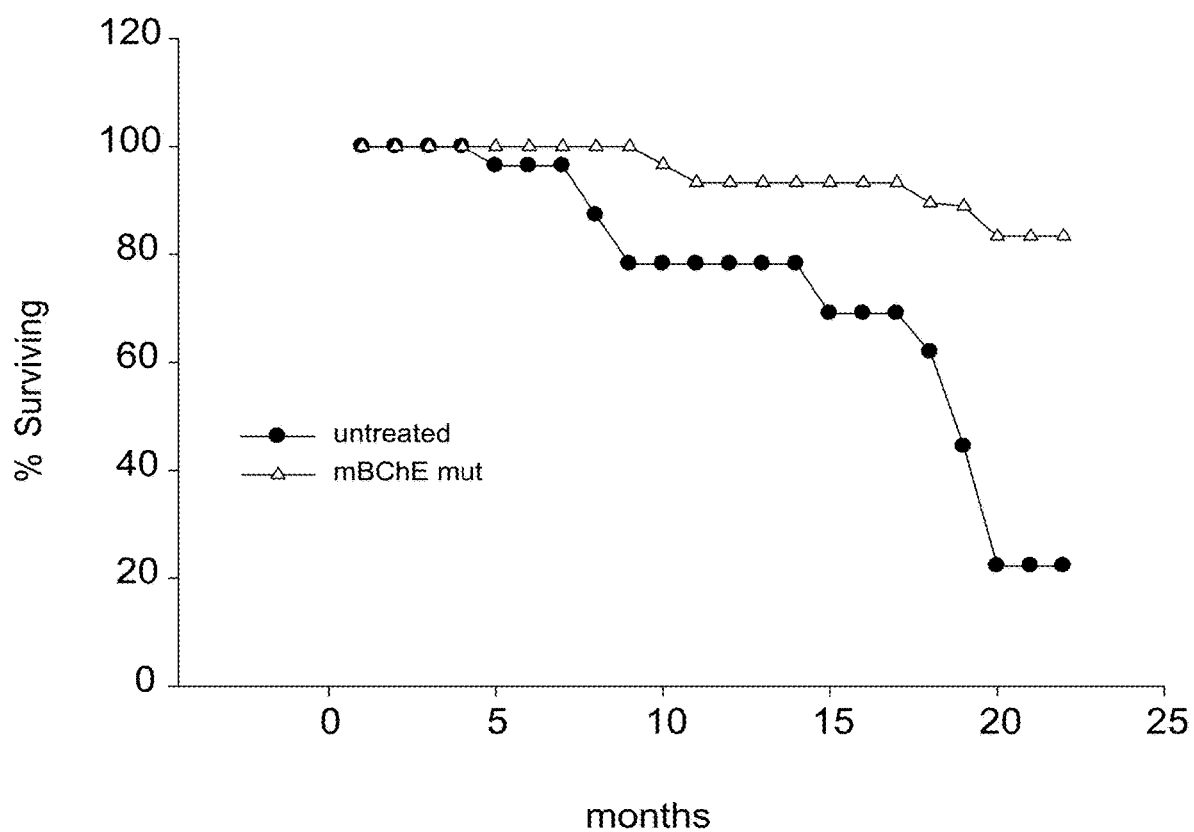

In another experiment, three month old C57/BL6 BChE knockout mice were tested for aggression. The knockout mice exhibited no detectable BChE and exhibited moderate elevation of ghrelin levels in the fed state (normal condition) and significantly higher aggression than wild-type mice of the same strain (FIG. 12).

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

---

What is claimed is:

1. A method for reducing the body weight of a mammal, wherein said method comprises administering nucleic acid encoding a polypeptide to said mammal, wherein said polypeptide comprises the amino acid sequence set forth in SEQ ID NO:3 comprising an F329M substitution and optionally one or more additional amino acid substitutions selected from the group consisting of A199S, F227A, S287G, A328W, and Y332G with the numbering starting after the signal sequence of SEQ ID NO:3, and wherein said polypeptide has an increased ability to hydrolyze acyl ghrelin as compared to a polypeptide having the amino acid sequence set forth in SEQ ID NO:3, and wherein the body weight of said mammal is reduced following said administration.

2. The method of claim 1, wherein said mammal is a human.

3. The method of claim 1, wherein said polypeptide comprises A199S.

4. The method of claim 1, wherein said polypeptide comprises said amino acid sequence comprising said F227A substitution.

5. The method of claim 1, wherein said polypeptide comprises said amino acid sequence comprising said A199S, F227A, S287G, and A328W substitutions.

6. The method of claim 1, wherein said polypeptide comprises said amino acid sequence comprising said A199S, F227A, S287G, A328W, and Y332G substitutions.

7. The method of claim 1, wherein said polypeptide comprises said amino acid sequence comprising S287G substitution.

8. The method of claim 1, wherein said polypeptide comprises said amino acid sequence comprising said A328W substitution.

9. The method of claim 1, wherein said method comprises administering a viral vector comprising said nucleic acid to said mammal.

10. The method of claim 9, wherein said viral vector is an adenoviral or adeno-associated viral vector.

* * * * *

UNITED STATES PATENT AND TRADEMARK OFFICE
CERTIFICATE OF CORRECTION

| | | |
|---|---|---|
| PATENT NO. | : 12,116,602 B2 | Page 1 of 1 |
| APPLICATION NO. | : 17/930943 | |
| DATED | : October 15, 2024 | |
| INVENTOR(S) | : Liyi Geng et al. | |

It is certified that error appears in the above-identified patent and that said Letters Patent is hereby corrected as shown below:

In the Claims

In Column 19, Line 20, In Claim 1, delete "and wherein" and insert -- wherein --.

In Column 20, Line 19, In Claim 7, delete "comprising" and insert -- comprising said --.

Signed and Sealed this
Tenth Day of December, 2024

Katherine Kelly Vidal
*Director of the United States Patent and Trademark Office*

SEQUENCE LISTING

```
Sequence total quantity: 4
SEQ ID NO: 1              moltype = AA  length = 603
FEATURE                   Location/Qualifiers
source                    1..603
                          mol_type = protein
                          organism = Mus musculus
SEQUENCE: 1
METQHTKVTQ THFLLWILLL CMPFGKSHTE EDFIITTKTG RVRGLSMPVL GGTVTAFLGI    60
PYAQPPLGSL RFKKPQPLNK WPDIHNATQY ANSCYQNIDQ AFPGFQGSEM WNPNTNLSED   120
CLYLNVWIPV PKPKNATVMV WIYGGGFQTG TSSLPVYDGK FLARVERVIV VSMNYRVGAL   180
GPLAFPGNPD APGNMGLFDQ QLALQWVQRN IAAFGGNPKS ITIFGESAGA ASVSLHLLCP   240
QSYPLFTRAI LESGSSNAPW AVKHPEEARN RTLTLAKFTG CSKENEMEMI KCLRSKDPQE   300
ILRNERFVLP SDSILSINFG PTVDGDFLTD MPHTLLQLGK VKKAQILGV NKDEGTAFLV    360
YGAPGFSKDN DSLITRKEFQ EGLNMYFPGV SRLGKEAVLF YYVDWLGEQS PEVYRDALDD   420
VIGDYNIICP ALEFTKKFAE LENNAFFYFF EHRSSKLPWP EWMGVMHGYE IEFVFGLPLG   480
RRVNYTRAEE IFSRSIMKTW ANFAKYGHPN GTQGNSTMWP VFTSTEQKYL TLNTEKSKIY   540
SKLRAPQCQF WRLFFPKVLE MTGDIDETEQ EWKAGFHRWS NYMMDWQNQF NDYTSKKESC   600
TAL                                                                603

SEQ ID NO: 2              moltype = DNA  length = 1812
FEATURE                   Location/Qualifiers
source                    1..1812
                          mol_type = genomic DNA
                          organism = Mus musculus
SEQUENCE: 2
atggagactc agcataccaa ggtaacacag acccacttcc tcctatggat tcttctgctc    60
```

```
tgcatgcctt ttgggaagtc acacactgaa gaagacttca taattacaac caagaccgga    120
agggtccgag ggctgagcat gccagttctt ggtggcacgg tgactgcctt tctcggtatc    180
ccctatgcac aacctcctct gggtagccta agattcaaaa agccgcaacc cttaaacaaa    240
tggcctgaca tccataatgc cactcaatat gcaaattctt gttatcagaa catagaccaa    300
gccttcccag gcttcccagg gtcagaaatg tggaatccaa acacaaacct cagtgaagac    360
tgcttgtatc tgaatgtttg gattccagta ccgaagccta aaaatgccac tgtcatggta    420
tggatctatg gtggtggctt tcaaactggg acctcttctc tacctgttta cgatgggaag    480
tttctagctc gtgttgaaag agttattgta gtttcgatga actataggg aggtgctcta    540
ggattcctag ctttttcccgg aaatcccgat gctccaggaa acatgggtt atttgatcaa    600
cagttggcac ttcaatgggt ccaaagaaat atagctgctt ttggagggaa tcctaaaagt    660
ataacgattt ttggagaaag tgcagggca gcttcagtta gcttacattt gctctgcccc    720
caaagttatc ctttgtttac cagagccatt cttgaaagtg ctcctctaa tgcccctgg    780
gcagtaaagc atcctgagga agccagaaac agaaccttga cctagctaa atttactggt    840
tgctcaaagg aaaatgagat ggagatgatt aaatgccttc gaagtaaaga tcctcaggaa    900
attcttcgca atgaaaggtt cgttctcccc tctgattcca tcttatccat aaattttggt    960
ccaacagtgg atggcgattt tctcaccgat atgccccaca cactactcca actaggaaaa   1020
gtgaaaaaag ctcagatctt agtgggagtt aacaaagatg aagggacagc tttcctagtg   1080
tacggtgctc cgggtttcag caaagacaat gatagcctta tcacaaggaa ggaatttcaa   1140
gaaggtttaa atatgtattt ccctggagtg agcagattgg gcaaggaagc agttctttc    1200
tactacgtgg actggttagg tgagcagtca ccagaagtct accgtgacgc tttggatgat   1260
gttattggag attacaacat catctgccct gcactggagt ttaccaagaa attcagag     1320
cttgaaaca atgctttttt ctacttttt gaacatccgct cttccaaac accttgga      1380
gaatggatgg gagtgatgca tggctatgaa attgaattg tgtttggctt accctctggga   1440
agaagagtta attatacgag agctgaggaa atctttagtc gatccataat gaaaacttgg   1500
gcaaattttg caaatatgg tcaccccaat gggacccagg gcaatagcac aatgtggcct   1560
gtcttcacaa gtactgaaca aaaatccta acattgaact acagagaagtc aaaaatatac   1620
tctaaacttc gtgctccca atgtcagttc tggagactat tttttccaaa agtcttggaa   1680
atgacaggag atattgatga aacggagcaa gagtggaagg caggatttca tcgctggagc   1740
aattacatga tggactggca aaatcaattt aacgattaca ctagcaagaa agagagctgt   1800
acagctctct aa                                                      1812

SEQ ID NO: 3              moltype = AA   length = 602
FEATURE                   Location/Qualifiers
source                    1..602
                          mol_type = protein
                          organism = Homo sapiens
SEQUENCE: 3
MHSKVTIICI RFLFWFLLLC MLIGKSHTED DIIIATKNGK VRGMNLTVFG GTVTAFLGIP     60
YAQPPLGRLR FKKPQSLTKW SDIWNATKYA NSCCQNIDQS FPGFHGSEMW NPNTDLSEDC    120
LYLNVWIPAP KPKNATVLIW IYGGGFQTGT SSLHVYDGKF LARVERVIVV SMNYRVGALG    180
FLALPGNPEA PGNMGLFDQQ LALQWVQKNI AAFGGNPKSV TLFGESAGAA SVSLHLLSPG    240
SHSLFTRAIL QSGSFNAPWA VTSLYEARNR TLNLAKLTGC SRENETEIIK CLRNKDPQEI    300
LLNEAFVVPY GTPLSVNFGP TVDGDFLTDM PDILLELGQF KKTQILVGVN KDEGTAFLVY    360
GAPGFSKDNN SIITRKEFQE GLKIFFPGVS EFGKESILFH YTDWVDDQRP ENYREALGDV    420
VGDYNFICPA LEFTKKFSEW GNNAFFYYFE HRSSKLPWPE WMGVMHGYEI EFVFGLPLER    480
RDNYTKAEEI LSRSIVKRWA NFAKYGNPNE TQNNSTWPV FKSTEQKYLT LNTESTRIMT    540
KLRAQQCRFW TSFFPKVLEM TGNIDEAEWE WKAGFHRWNN YMMDWKNQFN DYTSKKESCV    600
GL                                                                  602

SEQ ID NO: 4              moltype = DNA   length = 1809
FEATURE                   Location/Qualifiers
source                    1..1809
                          mol_type = genomic DNA
                          organism = Homo sapiens
SEQUENCE: 4
atgcatagca aagtcacaat catatgcatc agatttctct tttggttttct tttgctctgc     60
atgcttattg ggaagtcaca tactgaagat gacatcataa ttgcaacaaa gaatggaaaa    120
gtcagaggga tgaacttgac agttttggt ggcacggtaa cagccttct tggaattccc     180
tatgcacagc caccctcttgg tagacttcga ttcaaaaagc cacagtctct gaccaagtga    240
tctgatattt ggaatgccac aaaatatgca aattcttgct gtcagaacat agataccagt    300
tttccaggct tccatggatc agagatgtgg aacccaaaca ctgacctcag tgaagactgt    360
ttatatctaa atgtatggat tccagcacct aaaccaaaaa atgccactgt attgatatgg    420
atttatggt gtggtttca aactggaaca tcatctttac atgtttatga tggcaagttt    480
ctggctcggg ttgaaagagt tattgtagtg tcaatgaact ataggggtgc cctaggagga    540
ttcttagctt tgccaggaaa tcctgaggct ccagggaaca tgggttttat tgatcaacag    600
ttggctcttc agtgggttca aaaaaatata gcagcctttg gtgaaatcc taaaagtgta    660
actctctttg gagaaagtgc aggagcagct tcagttagcc tgcatttgct ttctcctgga    720
agccattcat tgtttaccag agccattctg caaagtggat cctttaatgc tccctgggcg    780
gtaacatctc tttatgaagc taggaacaga acgttgaact tagctaaatt gactggttgc    840
tctagagaga tgagaactga ataatcaag tgtcttagaa ataaagatcc ccaagaaatt    900
cttctgaatg aagcatttgt tgtccctat gggactcctt tgtcagtaaa ctttggtccg    960
accgtggatg gtgattttct cactgacatg ccagacatat acttgaact tggacaattt    1020
aaaaaaaccc agatttggt gggtgttaat aaagatgaag gacagctttt ttagtgtat    1080
ggtgctccg gcttcagcaa agataacaat agtatcataa ctagaaaaga atttcaggaa    1140
ggtttaaaaa tatttttcc aggagtgagt gagtttggaa aggaatccat ccttttcat    1200
tacacagact gggtagatga tcagagacct gaaaactacc gtgaggcctt gggtgatgtt   1260
gttgggatt ataatttcat atgccctgcc tggagttca ccaagaagtt ctcagaatgg   1320
ggaaataatg ccttttctac ctattttgaa caccgatcct ccaaacttcc gtggccagaa    1380
tggatgggag tgatgcatgg ctatgaaatt gaattctgtc ttggtttacc tctggaaaga    1440
```

-continued

```
agagataatt acacaaaagc cgaggaaatt ttgagtagat ccatagtgaa acggtgggca   1500
aattttgcaa aatatgggaa tccaaatgag actcagaaca atagcacaag ctggcctgtc   1560
ttcaaaagca ctgaacaaaa atatctaacc ttgaatacag agtcaacaag aataatgacg   1620
aaactacgtg ctcaacaatg tcgattctgg acatcatttt ttccaaaagt cttggaaatg   1680
acaggaaata ttgatgaagc agaatgggag tggaaagcag gattccatcg ctggaacaat   1740
tacatgatgg actggaaaaa tcaatttaac gattacacta gcaagaaaga aagttgtgtg   1800
ggtctctaa                                                           1809
```